(12) United States Patent
Yoon et al.

(10) Patent No.: US 11,457,635 B2
(45) Date of Patent: Oct. 4, 2022

(54) PSEUDOMONAS AERUGINOSA BACTERIOPHAGE PSE-AEP-3 AND USE THEREOF FOR INHIBITING PROLIFERATION OF PSEUDOMONAS AERUGINOSA

(71) Applicant: Intron Biotechnology, Inc., Gyeonggi-do (KR)

(72) Inventors: Seong Jun Yoon, Seoul (KR); Soo Youn Jun, Seoul (KR); Jee Soo Son, Seoul (KR); Hyoun Rok Paik, Incheon (KR); Hee Jeong Shin, Gyeonggi-do (KR); Sang Hyeon Kang, Seoul (KR)

(73) Assignee: INTRON BIOTECHNOLOGY, INC., Gyeonggi-Do (KR)

(*) Notice: Subject to any disclaimer, the term of this patent is extended or adjusted under 35 U.S.C. 154(b) by 565 days.

(21) Appl. No.: 16/486,592

(22) PCT Filed: Jan. 11, 2018

(86) PCT No.: PCT/KR2018/000507
§ 371 (c)(1),
(2) Date: Aug. 16, 2019

(87) PCT Pub. No.: WO2018/151416
PCT Pub. Date: Aug. 23, 2018

(65) Prior Publication Data
US 2019/0359948 A1    Nov. 28, 2019

(30) Foreign Application Priority Data
Feb. 17, 2017    (KR) .................. 10-2017-0021315

(51) Int. Cl.
A61K 35/76    (2015.01)
A01N 63/40    (2020.01)
(Continued)

(52) U.S. Cl.
CPC .............. *A01N 63/40* (2020.01); *A61K 35/76* (2013.01); *A61K 45/06* (2013.01); *A61P 31/04* (2018.01);
(Continued)

(58) Field of Classification Search
CPC .......... A61K 35/76; A61K 45/06; C12N 7/00; C12N 2795/10231; C12N 2795/10232; C12N 2795/10211
See application file for complete search history.

(56) References Cited

FOREIGN PATENT DOCUMENTS

| KR | 20120067096 A | 6/2012 |
|---|---|---|
| KR | 20130087118 A | 8/2013 |
| WO | WO-2018/151416 A1 | 8/2018 |

OTHER PUBLICATIONS

Alves, D. R. et al., "A Novel Bacteriophage Cocktail Reduces and Disperses Pseudomonas Aentginosa Biofihns under Static and Flow Conditions", Microbial Biotechnology, 2016, vol. 9, No. 1, pp. 61-74.

(Continued)

*Primary Examiner* — Allison M Fox
*Assistant Examiner* — Qing Xu
(74) *Attorney, Agent, or Firm* — Ballard Spahr LLP

(57) ABSTRACT

The present invention relates to *Podoviridae* bacteriophage Pse-AEP-3 (accession number: KCTC 13165BP) isolated from nature, the *Podoviridae* bacteriophage Pse-AEP-3 having the capability to specifically kill *Pseudomonas aeruginosa* and having a genome represented by SEQ ID NO: 1, and a method for preventing or treating diseases induced by *Pseudomonas aeruginosa* by using a composition containing the *Podoviridae* bacteriophage Pse-AEP-3 as an active ingredient.

1 Claim, 2 Drawing Sheets
Specification includes a Sequence Listing.

(51) Int. Cl.
*A61P 31/04* (2006.01)
*A61K 45/06* (2006.01)
*C12N 7/00* (2006.01)

(52) U.S. Cl.
CPC ...... *C12N 7/00* (2013.01); *C12N 2795/10231* (2013.01); *C12N 2795/10232* (2013.01); *C12N 2795/10271* (2013.01)

(56) References Cited

OTHER PUBLICATIONS

International Search Report and Written Opinion were dated Apr. 26, 2018 by the International Searching Authority for International Application No. PCT/KR2018/000507, filed on Jan. 11, 20018 and published as WO 2018/151416 on Aug. 23, 2018 (Applicant-Intron Biotechnology Inc.) (Original—8 Pages/ Translation—2 pages).
NCBI, GenBank Accession No. KR054029.1, "Pseudomonas Phage DL54, CompleteGenome", Mar. 16, 2016.
NCBI, GenBank Accession No. HG518155.1, "Pseudomonas Phage TL Complete Genome",Jan. 6, 2014.

[FIG. 1]
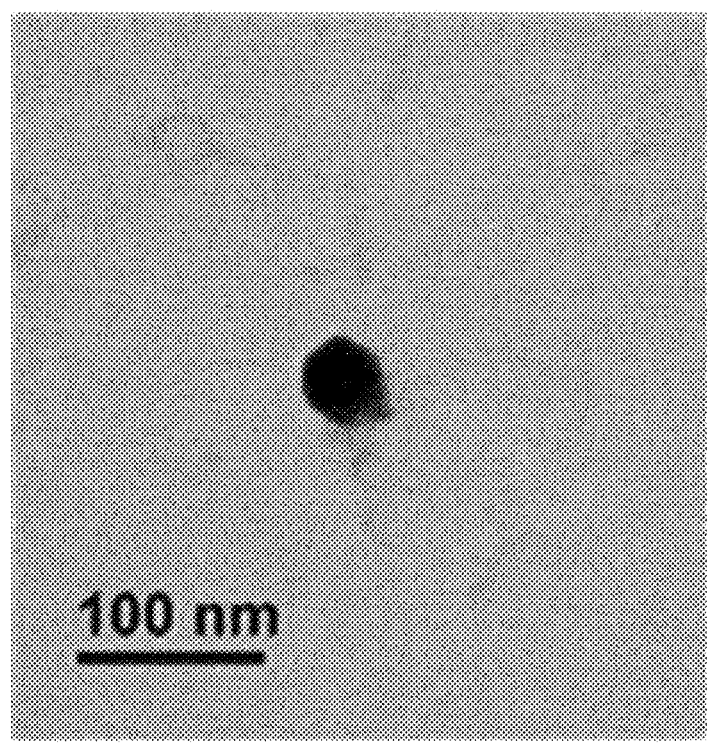

[FIG. 2]
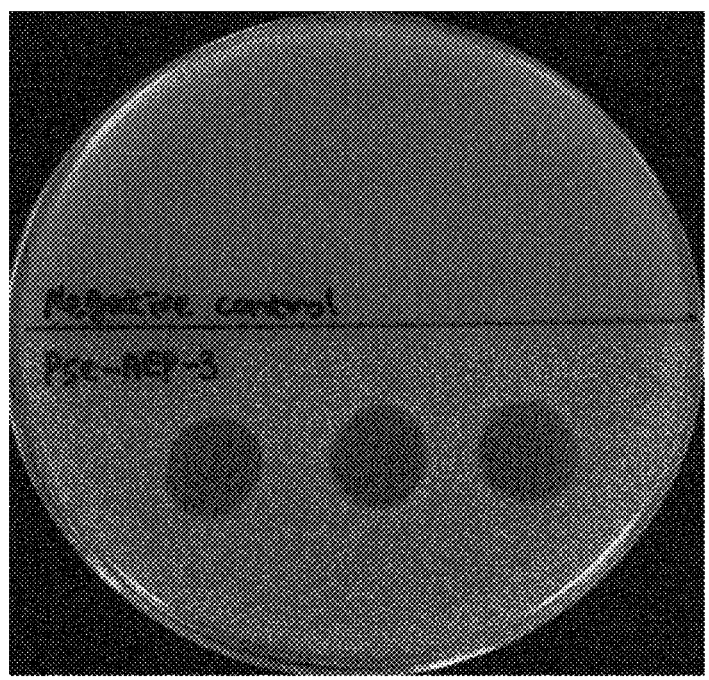

SEQUENCE LISTING

```
<160> NUMBER OF SEQ ID NOS: 1

<210> SEQ ID NO 1
<211> LENGTH: 45213
<212> TYPE: DNA
<213> ORGANISM: Pseudomonas aeruginosa bacteriophage Pse-AEP-3

<400> SEQUENCE: 1
tgatgacccg acgttgtagc caggtctaac ccaacgggcc ctgtcgggcc ccgttgtttc      60
tccgtaggga ctacatcatt agccatccaa ctgactttgc aattgacgaa gaccttgggc     120
tctttatccg aggataccga gaatcctgta cagcactcct agtccgtcac gcaagagcgc     180
cactctgtca acagataacc gaaaggataa tatgcgcaag gtagcaagta gtacaccccc     240
ctggttaagt cctacggcct acgtcgccgc gtctgaaggt ggaccatcg accttaacct      300 tcggttgtga cccagaccat gccgcacgat ttacccgttg gggcttaatc gaatcgagat     360
aaatggatac ctctgaggca cgggtgtaat gaatggctac gatcaataac gtaactgatc     420
tcgctattgc tgctatccag tggtctgacc gtcaggatct tacccaagaa cttctgatgt     480
tgttcattgg gaacactact gaccgtctta accgattgct acgaggaggg agaacgaaca     540
cttcgaaact ctcatggcct tcggtggtgg cattgagatc cctgagcact ttgttgctct     600
aaggtctatc aggggtctc tctctatcgg tggtcgctac tctctcagta catcacccaa      660
gatatcttca cccactatgt taactacaac taccaacctc agggtgtaac tactacactc     720
ggttgtgtaa cttcgttggc gtgcattgcc gttgttcgac ggtcccgttc attgcgaagt     780
cactgtctgt actctctaga gctgagacct ccctaacaaa ccgtcgttga gccagagcta     840
ggatccgcag atgtatccat ggatgtactt gatcggatct gagtatctgt acaccatgga     900
tgaagctcgg tcccagttct ggggtcagaa actcgaacgg gctgttatgg aactccagaa     960
```

```
cgaggagaat gccgctgact tcgctagcac tcgactggcg atcaaagaca ttgaacgtta    1020
aggagcttca gatgcctatc tttctaaaaa ccctcgcaat caaccttctg gctaccctct    1080
tcccaaccaa ggtaatcgct aagtctatcg tgactggagc taaggccctg gcagagaaga    1140
ccaactccaa ggttgacgac gagttcgtaa aagtcctgga agacaacctt aaggagaaga    1200
cggaggatgc aacttctaac tgataacctg gcagcatcg tcagtgccct ggtcgtatcc     1260
tcggtagtga cggtaggttc ctcggttgtc ggtcagaatg ttcatcaggc tctgcttgaa    1320
agaaacatcc aggccacgga gaagctcacc caagcggtga gcgaactcca gatttctatg    1380
gcaatctttg gggagcggta tgtcacccga aaagaaatga agaagagat aaaggaggcc     1440 aagaatgggt cttgaggtcg caacttatat taaccagttg gtgcctacga accctaccgg    1500
ctctgatctg aaatcctttg gggatgacca cctgcggctc attaagagtg ctattaagaa    1560
taccttcccc aatatttctc aggctgtcac tgtaacggca gcccagctaa acgcagtcgc    1620
tgatacaacc cagtatgtta agcctgggat ggtaatcatg tgggctgggt cattagctca    1680
gatcccagca ggttggaagc tttgcaatgg ggtaggtact acctctaacg ggattcctgt    1740
ccccaacctc attggtgcat tcccttgggg tatcgatggt acttcacagg ctgtaggtac    1800
tagaggtggt agcgctaaca ttgtatggga tgggttcact gaagggactg cccttaccct    1860
agcccagatc ccagcacaca cccacacttg gagatcccga ggggctacta ctctaactgg    1920
atctgcgggt gactcgggtg ctctaacggg tggatctggt aacgcagcca ataccaatct    1980
agagactggt cctgctggtc aaggtcagac tcacaaccat gcagtaaaga tcaacatgcc    2040
gttgggtaat atcccaccgt tctgttctgt gttcttcatc attaagaact gaggtataca    2100
atggccctag agagacaaga ggtcaagaac cctacgggga ttgtgaccga tatcaccccc    2160
gctgacctgc cactggagaa atggtccttc gggaacaacg tccggtttaa gaacggcaag    2220
gctcagaagg ctctgggcca tacgcctatc ttcgatacag cccaggcccc aatcttggat    2280
atgtttcctt tcatccggaa taacattccc tattggctcc tgtgttctga acaaaggttg    2340
tatctagccg acgggactac aatcatcgat gtatccccag gaccttactc tgctagtata    2400
actaacaggt ggtctgtagg gtcgttcaac ggggtaatct ttgctaacga tggggttaac    2460
cctcctcatc atcttccacc gtcagaatca acctttaggg tactccctaa cttcccagcg    2520
aatactactt ttaagaggct taagtctttt aagaacttcc tggttggctt aaacgctaca    2580
agtaactctg tagaaatgcc acagatggtc tggtggagta cttcggctga tgctggtggt    2640 gtaccegctt cttgggaccc aacgaccct actaaggatg ctggtcagaa caccttggct     2700
gataccaatg gtgctatcgt ggatggtgtg aagcttcgtg actccttcat catctacaag    2760
gaagactctg tatactccat gcggtatatc ggtggactgt atatcttcca gttccagcaa    2820
ctgtttaacg acgtgggtat ccttggtcct aactgtgcaa tagagtttga tgggaaccac    2880
tttgttgtag gtcacggtga tgtatatgtc cacaacggtg tgcagaagca gtctgttatt    2940
gatgcccagg tccgtaagtt cttcttctcg gatattaacc ctgacaacta tcaacggaca    3000
ttcgtacttg cagaccacgt gaatactgaa atgtgggtat gctactcttc cactaggtct    3060
gagccaggta agcactgcga cagggctatc atctggaact ggaaggaaaa cacttggagt    3120
atccgagatc ttcccaacgt tctcagtgga gcctacggga tcatcgatcc taaggtgtct    3180
aacctctggg atgacgaccc caaccctggg gataccgata cttcggtctg gggtgaaggc    3240
tcttataacc cagcaaagtc cagtatgatc ttctcgtctt tccaggataa gaagttgttc    3300
```

```
ctctttggta ataactctac attctctgga cagaacttcg tcagtaccct tgagagatcc    3360
gatatctatc tagggqatga tcgaatgatg aagacagtga gtgccatcat tccacacatt    3420
actggtaacg gtacttgtaa catctgggtg ggtaacgctc aggtacaagg ttctggtatt    3480
cgatggaaag gcccttaccc ataccggatt ggtcaggact ataagattga cactaaacat    3540
gtgggccggt atatagcctt gaagttcgac ttctcttcgg aggggqattg gtacttcaac    3600 ggatacacta ttgaaatggc cccgaaggca ggtatgcgat gagtcaaaag tacagccctt    3660
cgattccacc acaggaagag gaggaactgc tgcccttcct taatgaagaa ttcgttaggg    3720
ttggacagac tcttaatgac ctagctgacg gctactgggg ggtctctatg gagcccccta    3780
agaagctcaa gccagggact gtaaagtatt ttgcccccgg agtggtaggt ccagtatccg    3840
gcatctatca ttacgacttg gataaccaat ggagactcgc aggtactaaa cccaaggacc    3900 tgccgqqqqa ttttatccta tttaccccac agaacaacca tcagccgatg ggtacctgtg    3960
cctataggat gaacactgct aaggatgaag tatggataac catgctcatg tctggtggta    4020
actacactaa cggggctact gtcctggatc taccccaggc gtattggcct cctgctgagt    4080
tgtttatccc ggcctattcc agcatcatcc cagcgcagag cactattact tatccacctc    4140
cgtctgaccc taacgcacct ccgttggatc aagtctttga tgttctcaac agggctacta    4200
ttcagactgg ggtggttaac caagcaatgt ttaagatcac agctaatggc cgtgttctaa    4260
tccaaggaat tcccccaagga gcagtcttcg ggggtacatt cacattcccc ctggtggtga    4320
ctccatgatt catttgatta cccgtgagaa tatcgatctg cttcctaccg tagtccctgc    4380
tctggcccga gccttcaata ggacggacct cggtaagttt tgggacttcg aacacttggt    4440
tcactccttg gttaactacg aggcctatgt cttctaccaa gaagagagtg gctacgctgg    4500
tgtaattcaa gtgtcccaag cacccctggg taacatcctt cacttcttct ggagtggtaa    4560
gatgcctggg aatgaaaccc cggtagatta ctcggaggta gacgacttcc tcggacagtt    4620
cgcccaacga gttaactgtc ggtttatcca atgcgaaggt cgtcggggct ggaagcctac    4680
cctagagaaa ctcgggtaca ccgaagactc cgtatccttc tatcgtgagg taactccaga    4740
tgaacttcct ccaatttaat gtaaagcgtc tgatggggtt cgatgtagag gatgccctag    4800
attctcgggc ttacaagggt ggtagtaaga agcaaaagac cacctctgtc tctacaccct    4860
atcagcaagg taactataat gaactactct cgggtgccag tgattggcta cataacgggg    4920
gctttgaccc caattacggg ggcgatccga actttgaccc ggtggctgac caaaatactc    4980
tccagcttgg tggcatcgaa gggctgggtg gtctcggggg tgcccttcag tctctcctgg    5040
gtagctcagg tgttagctct ctggctgatt accttggtcc ttacgatccc aacaaaactg    5100
gcttggcgaa cgccattggt gcagccaacg agcagatgca atgggacttc gacactacgg    5160
tacgtccaga cctgcgagca ggggccacta atgctggtca gtatgggagt tcccgagcgg    5220
gtgtagcaga aggtattgct accgctagat tgctccagaa tcaacagaat aacgcctccc    5280
agttggcttt ccaagaccag caggcttaca accagaatag gttgaatacc ctgggtaacc    5340
tgtcggctat tgctaagggc ctcggctctg gtaatgccat gcaggtagat gctggtagta    5400
tgcttcagaa ccaggagcag caggaaatca acgggqctct acagaagtgg gcctatgaga    5460
ataacgtcag cctcaacgac ctcctcgcct ataaggagct tatctccggc gatatggggg    5520
gaaccaacgt tactacctcc tcgggtggtg gcggtggtgg tggcctcggg tctgccctgg    5580
gtgctctcgg tggtgcttcc ttgggtgctc tcttcggtgg tccagctggt gcttctgttg    5640
gtatgaacgc aggtggtagg gtaggggqcc ttctcttcta atggcttccc tccctcagaa    5700
```

```
actgttcgct ataggacaga acataggtgg tgggcaggag cgggttcagt tgagtcgtca    5760
aggctcctac cgccccaccc accttgggac gatgcaatcg ggagagtcta gtggacaatc    5820 aaacccttt ggcgcaatgg gcggagcagc actcgcggct ctcctcgggc aaggaagtga    5880
gccttcttca gaagcagtac caagcttttc tgtcgagggg gctagaggag caagcgaacg    5940
aggcgcagcg gaagttgcag caggtatggg agcgggagtg ggaatccttc ctagcgcaga    6000
agaactcggt ttcggacagc agccaaagtc tggaatccta agtaaactat ttggaggtta    6060
atcctatggc cagcatggct tatgaagggt ccccaattcg ccctagcatc ctccgggctg    6120
ctcagaatga actggacatg gcgcgaatcg caaggaacaa actgccgctg gctgtagagg    6180
gctcaggaat ccctgatcgt gtccgccggg ctgctcaggc tgccctagag aaccctgacc    6240
gttggtctcg ggctgcccaa gaggtgaccc ctgcggctga agctacgggt cgtggtgccc    6300
tgggccgtat cgcaggtatc ctcggtggac cggtatccgt tggcatccaa gcggctgtaa    6360
ccccaggaga acttggggat gcagagcgta ctcgtgcaga agaaatagct caggctagtc    6420
aggctgtgga gaatatgggg cctgaggttg ctcaagaggc aaaccaatgg gcccagggtg    6480
taggccaacg tgcagcccag aacgccacag ggggccctac gggggctgaa ctcctgtcct    6540
atggggtaac ccctaaccaa ccctctatcg agcctgagat caccccagag gtggcttccg    6600
aggctggtgc tgctgtagca gatgaggagg aggctaatcg ccaggtcatc caacagggtg    6660
cagctgaagg tcttcgtact ggtgctgtaa gtcgtcctga aatggcccag gctgtagttg    6720
aagctgatgc ccagagagag ggtgtagagc ttaaacccca agagcttaag aaccgggtga    6780
acgaagagtt gacccagatg aggactatgg acaatgatga tctgtctcgt tatgtatctt    6840
acgctctcat tggtactggt cttctggctt cggccctaga caagactggt aaagccgggg    6900
atatgttcgc tgcttcctac gagcgtcagc tggatcgtaa cctacaggct gggatcaacc    6960
agcagaagat ggctgccgca gctgctgatc gtcagatcaa ggaaaaggat ctggagcgta    7020
aggtggctaa ggatgctgct gatgtacgtc taggcgaagg gaacctggag gtcaagaagg    7080
gaacccttaa ggaaacctct cgtaagaaca ctggtcttct ggataggtgg actgaggagg    7140
ctgctcgggg ccgagccaac cttgccctaa cccagcgagg tcaggatatg gctaaccaac    7200
gggcccagct acaggctgaa acaacccgtc gtggccagga tatgtctcaa gagaatgccc    7260
agcttagttc tgctgtacgt ctgaagactg ctaagattag cgctcaggca cgtcaggcag    7320
cagctaaggc agcccgaggt gagccggtta ctaccaaaga tgccttggga atcctcagtg    7380
aagtcagtgg atctcaggcc ttgggtggta agaagttggg taagactgcc caacaggcta    7440
tagctcagac ccttcgtaac gaaatgaggg ctaaccctgg ggctaaccct attggtatta    7500
tccagcggga ggctgctaag cttcaaccta cgggtaactg gttctttggt ggtgatctgg    7560
actatcctgc cccaacccga taaaaggtac ttgacaaagt atccaaaatg tagtataata    7620
gacctatagg ctcttaagat tccttcttcc ttttgactta cttactaaga aggttagtat    7680
cctaagatac atcttaagag cctattctct ttccagcaac tagaaggtga cttatggctc    7740
tttctccaga actgaaggcc gctattgatg cggaactggc tgaggtcaag ggcctcgacg    7800
tagccgctga attggcttcc ttgaatgagc cagaggttat cgaagaggca ccccaggaag    7860
tagctccagc tacccctgag cctgccccag acctgagtgc cctagtaact ccggctgacc    7920
ctaattctat tagctctgcg attggtcgcg gggttgatac catgcagtct aacatcggtg    7980
gtaccattgc tactctcggt gagttgactg gcagtgacta cctgaaagac tacggcacac    8040
```

-continued

| | | | | |
|---|---|---|---|---|
| agatggccga | agagaatgct | caggaagcgt | cacagtacgg | aaccccgat gttaggtcct | 8100 |
| tcgctgatat | ccaagatatc | ccatccatcg | gttcgttcct | caagaataac atcgtagagg | 8160 |
| cactcccctc | gatggctcct | gtcctggctg | gtggtgcagc | aggggctaag gctggctctg | 8220 |
| tatttggagc | cccaggtcgt | atgggtggtg | ccctcattgg | ttccttccta agctccatgg | 8280 |
| gtatcaacgt | gggtgccctg | agcaaccaga | tgaaggagct | agaccccgac caaagcaacc | 8340 |
| catggaccgc | agtcctaggt | ggtgctggtc | tgtctgccct | ggataccgca ggggctgggg | 8400 |
| ttatcgctgg | tccctgttg | aagcaccttg | ggaaagacgg | ggcataccat atgctggtac | 8460 |
| agtccggtct | acccaagcag | actgctattg | aagctgttac | ccaagctggt aaacacgctg | 8520 |
| tagtctctgg | tgtggctgaa | ggtgttacct | ctggtgccca | gcaggccctc caggacacta | 8580 |
| tcgcgtatga | tgccgttggg | cagacccaat | cccctgagca | gttcatggat aacctcctga | 8640 |
| cggctgcatt | cactggtact | gctatgggta | ctgccggtgg | tgctgtatcc tcggggatgg | 8700 |
| acaccctggg | tcgtcatcag | gactccgctg | gatctgctgt | ggttgatcct aacgccctg | 8760 |
| cggcccctcc | taaggcttct | gagtttgagc | ctaggggtac | ggtcaagaag gcttgggatg | 8820 |
| ccctaggaaa | cgaagctacg | tcgctcctag | agccactcgc | taaggcctcc cctatcgctc | 8880 |
| gtgagttctc | tgagaccttc | cgtgctgata | tgagtggtaa | gcgggcctct ggtaagacta | 8940 |
| tctttgagga | ccaggaacta | caggcaggta | agtggaactc | tgaactagat aacatctttg | 9000 |
| agggtaagtc | ttccaaagag | atcgatagga | ttatcgctga | tacatccgct ggtgtcaaca | 9060 |
| cccccgaggc | tacccgtcta | cgttctttga | tggatgacgt | aaggaatgag gctgttaatc | 9120 |
| gtggtggcat | gtctgttggg | accatcccca | actatatgcc | ctttggggttg tcccctgaga | 9180 |
| aggttcaatc | tccagagttc | ctgaacgaca | ttactccgta | cttccagaac cgacaagctg | 9240 |
| ctgaagatgc | tgtagctaac | tggctggttg | aagtctcgga | tgatactcgt ggtaacactg | 9300 |
| cccctgaggt | taaccgattg | gttactcaga | accagcagac | cggggcttgg gaagtagacc | 9360 |
| ctcgctaccg | tatccagggt | gatccggata | cccttcgtgg | acggtttgcc cagagtgatg | 9420 |
| cagtacctaa | gtatggtcag | ctggaagaga | gtcgggcctt | tggctccgtg cctcaagaga | 9480 |
| tcctcaacaa | gtattctctc | aacgatactc | ctaagaagcg | tctccaggaa atccgagatt | 9540 |
| acttcgaagg | ggcttcccac | cggattgcct | ttaccgaacg | gtttggtatc aacggagaga | 9600 |
| aggctaacgc | taagattgct | tctgctgtag | ctgaggctca | acgggctggt aagagagtca | 9660 |
| ctaaggaaga | agtggatcgg | atgtatgacc | tagtggatgc | ctataatggt atgcacggtc | 9720 |
| gtatcaaaga | tcctaacctt | aagaagctag | cggctgttac | gtcgggtgcc ctcgtgctct | 9780 |
| ccagacttcc | cctcgccggc | ttctcgaccc | taaccgagtt | cagcctacca ttcgctaagg | 9840 |
| ctggggttat | gcctaccctt | ggggctgtac | tcccaaccat | gggtgaggta gtaaggcaag | 9900 |
| cagcccgcag | gatctacagt | ggggttccaa | agtctgagac | cggtcggttt atgagtgata | 9960 |
| tgaaccacac | cctggcctct | gctacctctc | tgatggctga | ccgggttggc gctgaggtgt | 10020 |
| ttaactctac | catccaaaag | gcgatccgtg | gtcagttcct | catcaacggc ttgtccatcc | 10080 |
| taacccatgt | taaccgagtc | tttgcaacag | agactgctaa | gcgggtctat cagaacaacc | 10140 |
| tgatggatct | agccgcaggg | ctccccttca | gttctgccaa | tggtgctctg aaggttgctc | 10200 |
| agcttcggga | aatgggggtt | aacatcggta | gccagcagga | tgccctcaag ttgatctccc | 10260 |
| cggctacccc | atctgaagtc | ctgatggcta | acaacgtcaa | gaccttggcc atgcgtcggt | 10320 |
| ttgtagatca | ggtagttctc | gaccccacct | tcgctgataa | gcctatgtgg atgagcaacg | 10380 |
| gaaacgttca | gatgttctcc | ctcttgaagg | gttacccagc | agcctatggt aacatcatcc | 10440 |

```
taccgatgtt ccgtagacga atgagcccac acttcgctgg ttcctggacc aacgctggta    10500
tgggtgccgc aggtgtagcc ttcactcttg gtctgatgat gagtctgggg tatctccagg    10560
atgagcttcg tcaactggct aagttcggtg ggtctagccg agaggatacc cgtagtccag    10620
aacaacggat gatggacgta gtgatgcaac agatgccact ccaggcttct atgatctacg    10680
acatgctgac gggttaccgt cgagggacta cccccgcaga ggtactattg ggtccagtag    10740
ctggtgctgc aactgagggt gctatggctg ttggtaaaac tatcgcttcg tttggggatg    10800
acccatccgc aggtgaaatc tggaagttct tgtataagca aactccagca cgtcctttcg    10860
ttgccggtat ggaagcgatg gaagatgctc tggatcttta aggagaagta atatggcaac    10920
ttatgtagaa actgatgccg ctggtcctgg tggccgtgcc tacgtggttg atgtgccaaa    10980
agtcttccga cgtaatgccg atggtgatct cattgagatt acctcggatg ccggtcgggt    11040
aaatactaac atcgttaccg ctacagagtt cctccctgac tattatgcag ttaaggagaa    11100
cgcagccctg gtagtagaga acgttacagc ctccttcccg gagaatccct cagaggccgt    11160
tatcccctct gtcctggtca ataccctcgt gggtgctcct ggagaaacct cgggtggtaa    11220
ccgtgacccct ggccacgtga ttggtctgtt ctctgagacc atgattgagg caccttgcgg    11280
tactgcattc ggtagtgaat ccgagtaga ccctcgacgg gaacacctgg gtgtttacgt    11340
ggctattaag cacgtgattg gcccggatga ccaaaacggt ggtaccatcg gggattacat    11400
tatcgagcag tttgacgaca tgcgtggtcc tgtgaagaac attggttctc ttcaacagaa    11460
ctacctggat ccccgactgg tgactactca cctcggtggt aacgttgtca cacccagca    11520
actcacccag aacattaccc ttactaagca gcagtctggt tggttcttca tgtcccaggg    11580
gactacggat attaccgtta ctcttggtcc ggatgtaacc ccaggttgtc acttccactt    11640
tatccaaggg tctacagcta agatcaagtt cgctgtatct ccggacaagg cttggtatgc    11700
taagggtaat cagacggaga ctgatggtca atttggggaa tgcactgtcc gagtgtatcc    11760
tttcggtggt accgtgggta ccttcaaatc ggcagtttaa taggagttag attatggcag    11820
gttatatcgc tgacaacgac ggcaacagtg tattcgttat tcaatcgaag gctattgctg    11880
ttcgtaatga ggatgggacc ctccgacaag tcattggccc gaaagacttt gagccagtga    11940
agtgggagga tattgagggg aagcctaagc ttctggaggt gggtgctaag gctagtgagg    12000
ctaaaccagg taactggaag cctaaggcta gcgaagtgag tggcctatat gaagccattg    12060
cggcttccat ccaggataag atatctgaga tccccgtggc ttcctatacg gatactcacg    12120
aggcactcgt ggataagttc aatacactac tgaacgctct ccggagctaa agataaggcc    12180
ccttgggata acacccttgg ggcctttttt tggttactcg acggggtggt agataggagt    12240
atcttcggat accctgtcca tgtggtcccg gatgaagcaa cagctatcct gtaggttctc    12300
gaagactaca ggaagggact ctagatatga gctgacacag tggatcccca tcccctgttt    12360
tctctgctcg aaattcctcc aacgaaacca ttgcttatac tgagggaaga gaacttccc    12420
cacttgcttc actcgatact tcataaggaa cctgcccaag ataacacttc gatgaggagt    12480
ctggatattt ctcccagggt caggagtaac atcagtcagc tatccctac atacaccagt    12540
agggcaaaca aagctgctac cgcaatgtag gtccaaggga atccaccctt acccttttga    12600
tcttctgca taaccctcc aatctccgta gaatacagaa gccctgaggt ctactagatc    12660
tagcatccct tcgaggaatt caatctgtct tttagcttct tcagccagtt cttcaagga    12720
aaaggccttc gcctcagcct tcgcaagagc gctttgcgtc tcttcaagtg ctttctccag    12780
```

```
ttcagccttt gtcatagtac accaccttgt cactgcccct gagaacatac tcagaatcaa    12840
tagtccaact catggtaggg catttgattc gaatcatctt cggagtaaaa ccatcaactg    12900
taccaatagc taggtgggag gaggtgttcc tgtggaccag gaagactaca ctgtcccta    12960 cctctagctt acgtcccact cgatctttca tagattaccc caagatatcc ggaaggtgaa    13020
cgctggggat gtagaggatc tccaggactt cgatggaata catccctcgc ctaagcccct    13080
cctcagcacc cccttccca aacttcatat ccagccagag ttctgcggag atcgcgtct    13140 taaacgccaa cccccgttga ccgaagtcat gctcagactt aatgtagtac aggtctggca    13200
agaacttact cacaggaact cctccacgct catcagcttg aggtcatact ctccatcctt    13260
gtggttccgg aggagggcta cacctcgcca gtggtcgtta ccctgcggtc ccttgtagga    13320
ctcatcgtgg gtatagaagc ttccgactac cagcccgtgg attcgcttct tacctactgc    13380
ctcgatgtgg tacttgaatc cttgctcatg gccttggacg aagctgcgct tgatcttatt    13440
gaggcgatgc tcggcactcc cgccgtatgg ccgaccactg ttgggattgt agaagtagtg    13500
ggcgaaggcg acaccttcga taacacccac gtcgaggaaa tcatggacaa tccaatcgga    13560
cagatcaaaa tgatcgtacc caataaaacc ttggagagca gggttagaat tttcataccg    13620
cttgatacgc tcctcgtggt ttccgatgaa gaagtgcatt tctggtcggt agatacgctt    13680
cttacaaccc gcttggtgtt gctgtaggcg gcgaagagga tcgagcagaa ctcgcatcgc    13740
atcattacca gcttgtatgt cagcgaggac tcgacggcct tcgatcttag cggtaccacg    13800
gtcgtagctt gacagactgg gcatgtccca atggtcccca atatgaacaa ttcgcttggg    13860
gcggttacgt gcgatccact ccccaaggtt cccgaggtga tcgatgttga cctcggatcg    13920
aacttgggtg tccgcaatga cgagagtgtc ttcattatac ttttttactca ttagggaagg    13980 actccttgaa agtctctaga gtaaaccagc ggaatccgtt acgttcggcc cattccgcca    14040
tggattgctt tgtgccatct ttacgcttac taagccaatg gcaagctgtg ttaggacgct    14100
cgaagataaa cacaagttca gtatctgggg ggagagcctc cctcacccag atgtacttag    14160
atgcctccga ggcttcctgg aagtacccct taacctctac caacaggtgc ttcgtcgatc    14220
cacaaggttg tgaggtcgat accttgaagt cgggcttgta cttgtgctgt atgacgtagc    14280
tcaccgggtc tggcttgaac tgcatccagg gcatcgtctc gtggacgatc ttctcggttt    14340
cgctgtcgta cttcgtccca atcaatgact tcagtttggg tctgaagaat ctcccctgct    14400
ttgccaatga gccctccttc ttgaagcttc cagataaccg agagtgtccc ttcagtcagg    14460
atagaattag cccgaaccag aagccagatc caatccccca ggcacacccg gaactccgga    14520
tacttcagtt tgatacgttg gatatgagag acaaccttt caacttggtt gtcagttagg    14580
ggctgagagt gatccagaag agggtctaaa actcggttaa gagtaatgca cttctcttct    14640
ttatcaaact cataagccct tgaacggtag atttgagatt tcagtccacg gatacttatg    14700
ggccagcatg aaatctcaca cagtcctaca tcgaactctg ctggatggga gtgagtactc    14760
acgacaaggt tgacgggtag gtcaacacca atggattccc acacatcaaa ccccgcagga    14820
tacccatcag gcttatcccc agtcctacac cggaccttct tgtggcccag cttgttgtag    14880
aatcgagtga cctctacctc tagggtatcg tcatacagg ggatcaaccg cggtccaaag    14940
cgactacgcc gagtatcagt ggggtcctcc acgtatggcc tacggacata gaggtcgata    15000
tccttgggtg caacccgtt gtctgcatcc cgaaggaaac caccagcgac cttgtagtca    15060
gtaaagttaa gaccctcaag gatctcaaag aggccttcac agattttctg tgcttcctca    15120
atagaatatt tcttcatcgt cataggaat ctcccaatgt ttcttcagtg agcagtgata    15180
```

```
ctcgttaccg gactgctgaa tatcaagcca agagcggtcc cgaatgaggt agaggagacg    15240
aaaattctcc agaaggtact ctttccaatt atctccgtac ttctgttggt aggcgtaagc    15300
gcaagctgcg aagagatctc tctcactaga aagctcccca agcaaatctg ccgctgtctt    15360
tggtcccgtc cctgggaggc ctggtatgtt atccacggag tcaccaacaa ggagttgccc    15420
gtagaggaat gccgtaccgt tgccctcaag cttccatgat ttctgcggct tcttaacacc    15480
atacattctc caagaagcgg agactcttcc aagaccatca acttgaaacg gtcccaactc    15540
cggctgggaa tctccacagg gccaactgta atggtagcat cctgggactt ggcggatatc    15600
cttgtctcta gaacacgctg taaagttaac tccctcttca gtgcctcgaa tcccgagcca    15660
gtcatcagcc tcgataccgt ggaaagtgat tgctccccac ttgtccttaa gtctggctga    15720
cacggtttcc cagtgatgag gcttttcaag accgattcga gtacccttat attgcttgat    15780
tttcgcaagc tccagcctaa aatttccttg gccagtaagg tagatttcac actcatctgc    15840
attcacccTT tgataatTT gttcgacttt atcatcgacg agcttgtgga cttcttcctc    15900
aggccagggc ttctccactt ggatatcgaa gatgtgttcc ttcgacatag ccacgtggcc    15960
tagctcatac ctaagaacgt caccatcgat accagcaatc atcacgttac ctcttctacg    16020
acctgagact ctttgagctt ctcttcccag aagacacgaa gggcaaaggc ttcacccttg    16080
gctcgatact ctgggtgctc taccaccggg ttaaccagtg cctcatagcc cttccagtcg    16140
taatattcac tttcttgacg cttggccttg tccatagctt cctccgttag gctgtagcct    16200
ggaggaagcc ccaggtctac atcgatgccc attacagagt agttactagg aacagtctta    16260
gcccttggat ccaacagaag ttccattgga gtcctcctct tgctgaatga cgagttccag    16320
ggacgctagg gcgttccaca cttcgtgata ccggtggggt agcttacttt ggggtccaa     16380 agcctcaccc ttgtgtcgct caaggaggtg tctcccgaag gcagcatcat atcgctggac    16440
tccgttctcg acagacctcc aaccccgcg actatacttg ctggctccga agttagcaac     16500
ttgtgccact gcatatagag ccctcgggaa cgcttcgaag atgattccaa catccacctt    16560
gccgctatca gtttagcgc ccggctcacc cggcttgatt ccattaggat cgacctctac     16620
tttattatta gatgcagctg tagaactgac caccttaca ccccacactc tctcgaattc     16680
aattaagcag taggggcagc ccaatgggca taccccgcc tcgtgatcct ccaagccctt     16740
agataggagc gtcttcgtca tcgaatacct cgtcgaatac atcctcgggc tcttcctcgg    16800
tgaaggcacc accgaacagc ggatcatcct caccgtcacc accggataca atctcgtgga    16860
gtcgtacacc gcgcagtcgc agggccgtca tagtaccctt gcctcgtggg cccttttggg    16920
tctcgatcag gatgccaact tcaccagtag atccacccca cgggttgggg ccatcatacg    16980
gcttgttgtc cgaggtcaga accaccggct tcattacagc agacttccgc tcaccatctt    17040
gcatccaatc cacgtgcttc ttctgcttga ccttgaacag gtactcgccg tcacgctctt    17100
ggtacttgat ggtacccttc agtcgggcat ccttggactc catctgctgt accagatcgt    17160
cggcctcttc tttggtcgga atgcagatgg ttacttggta gacttcaccg tactcggtgt    17220
ccggagttac gatgtagggg aagatcagct tcgctaccgg gaaggtgaat cgttgggata    17280 cttttcttaga catatcttaa acctctcgta gggaagaagg tattatacca caaggggc     17340 tgaaagtcaa ccccccagatg tatcagtgtg tgtcatacca cgagcgacca gcgatggaat    17400
cactggccaa aggacagtta accccaagga gcactccagc atcccggaca cagatttcca    17460
tctgtccacg tagcgcaatg agatcctctg ggtggcattc ccactgacct tcgtcatgga    17520
```

```
tatccaggac tttccaagcc cgaaggttca acctccggac ccgttcatct aggagcacca   17580
tggcccactt catgacaatt gcacctgccg cttggaggag ggtgttcaat gccttatgga   17640
tcatcacgtc gccagactca gaacgtcgca tggttagctt ccgtccgtct agcccttcga   17700
gataacctct ctcggcttcc tgcttaaccc tctcaatcaa tgcagcaagg tcagggttag   17760
cctcaaggaa ctgggcccgg agcctagccc catctgccct tgtgccccca ataatagtcc   17820
cgatcttggc atcccagca ccgtagatga aggcgtagat gaacgtctta gcatcgtcac    17880
gggttgggag acctgcggct atctggttgg ccgtgtgtac atcaccctcg accacctctt   17940
tggtgtactc tgggttattg atgtaggatg caagcatccg aagctctagt ccagcaccgt   18000
catagcccac gaagaccatt tgattcgctg ggacgtatac cttgtgcttt cctacaggct   18060
tccacttacc tttcttgagt tcctccacaa tgttagtgaa gggcctaacc ctttcgttct   18120
ctccaatgtc tcggcggagg acagtccatt tccattcacc ggcatcaggt gtccctgga    18180 acaaccctcg gatttctggt ccaaagggag aacgagcagc ggggatatta actactacac   18240
ggtgcctcat acgcccgta ggtgttgcac aggggttagc actcccctct aggcgtccat     18300
cgggcctcac ctgatcgaca agcccctgca gagggaccg tcggtgggcc caaaccattc    18360
gctgcatcac cagctttccc aggtctccct ggacggtatc catcgactct tccgtcatct   18420
tcggagtcgt caatacctt tcgttgccttt ctagctttct cttgacctct ccgatggtag    18480
tcttcccagg gatgattccc tggagcttca ttcggagtcg tccagattta ctctgtcgga   18540
gatcctcaat gtacttattc aaggactcat taaggtcgga tccacgtagc ttcttgccat   18600
cagttccgac agtaatatcc ttgatgttcc attggtcagg aatccatccc tgatccaaca   18660
tccaatcctt gaacttagca gtcttgccaa ggtcgaaggg aatgtactcg attgcagtga   18720
atggtccaga tacctcgaag tgcccaagac gttgccataa ggactggagc ctttgattcg   18780
gcttaccact cttttaggaat ggcttgctga aggccccagc ctttacgatc atcatcggca    18840
tctgggggac ggcctcaagg tcaatcttga ggattcgttc ggtaagcaca tggatcagcc   18900
acttggcccg ctgagtcttg aagtggactc cacgtttact ctggcgactg ataatatcag   18960
ctaccttgtg ctcaacgaac agtgactttc tccaatccac ttagtccccc ttaagacgct   19020
ccgccagatt ctctacgact acctccacgg cctcgtcgga gatacccctcc aggtaggaga   19080 ggtagtccac ggttccgctt cggtccagtc gccattgctg ctccaagaac gctacagcaa   19140
cttgcttgag caggaagtca tctacccgct ccatgagaac acttttgatc ttgctcatgt   19200
tatcaccagt cgaaaatgaa gtaggaacat ccacgctcac aggcgaggtc taccaggtac   19260
caggataggt caaccttgcg ctggatatcc ttgatatcac tcagttcttc atcggacaga   19320
ttgagggtat caccccgctt ctccttaagg aattgaaact cccatttctt ctcctcttgg   19380
gagacaacca gggtatcccg aggatccagc tgggcgcccc tgtccacgta gaagtcatcg   19440
tagaggctca tatccttgtc acgaatccgg gcgtttcgac gatccgagta ggaactcagg   19500
ttcaggtgag agcctgtgaa gtagctcacc cccaggaatc cctctggcag gctcaggaac   19560
acccgacgct tctcccgtag ggtaatgtgg ggactgctga ggaacttccg gatgttagtc   19620
ctttgtacct ccatgctctt atgtagggca gaagccatat tacacaggta cttaccacgg   19680
acatgtttgg agtagcttac atggtcactc atttgtatct cctataggg taaagcaacc     19740 cccggcacct taaggttatt atatcacact ttgctggatt tgtcaagact atttgtggaa   19800
aaccctgtca taccacttgt agaagtattg agcagaggta atcccaatag cacctcccca   19860
cccggacacg aagataaacc atccgatatc caagtgggag gaggctaccg ccttgatgta   19920
```

```
agcaaactga gccagcgtga tacaccaaga cactacgaac ccagccttga tcttgtcatc   19980
ccggagcagc ttagagttca atcccaggag gaatacctgg aagaatgcac tccagaagat   20040
gacaaggact tgtagagcta ttgacatgac tcgcatacct cgggatctag gccacaggca   20100
ctacccaagg ggaagtcatc agcatcgatc tcggggccac cccagctacc agagaactcc   20160
ttctccaggg caatctcctt ccgtgcctga tcctccaggc tttccttctt actcgccatc   20220
gttaatctcc tccacagaaa cccatccacg dacagcccca acctcgttgg cccgtacggt   20280
cattggattg gcatcggaat cacccaggaa gaaccgaatg atatccaact cgattcgata   20340
gaagtccgca gtgaacacct tggtgtcctg gaaccccacg ttaacccgat acttcttcat   20400
tcttacctcc caggagttct tcgaggttag ccagtacctt ctgggccttc aggttgtcct   20460
gcatgacctg ggtacgctca gccttaagca ggctaatctc gttgtagatg cgctcagact   20520
cctccgaaga ctcttggatg aaggtcttca ggttcaccag aaccttgtcg aaggagctaa   20580
ggatgttact gatgctaagc tttcggttaa acatagagag tcctcggggg cccgaaggcc   20640
cctccttagt tactttttct tacgaatgcc tttggcctta cgattgccca cacgaccacc   20700
atcagcagcg ttagaagaat gactacggac gcggagatta gaatccccgt taccgccacc   20760
atctttaaca cgtttgatat gatcgacaac ctcatcggct ccgagtttcc ttccaagacg   20820
cttttccacc tttcggcggg ctcggtgccg ctgagcatct ccagacttag ccccacgcc    20880 cgtttcgccg cgtcgaatag ccagttccct ttcacgcttg tagttcctca ctcgcttttt   20940
agccaatcta cagtcctcca ttcaacaagc tcttgccaag tcatgccgag tacccggagg   21000
aggtagttga acagtgcgtg actgaccact ccatcctgaa ggcaatactc aaacatttct   21060
tcggagaact tggagaagtc gttgaaatca cccttgtgac acttcaggaa tctaccccag   21120
gcacccaggg aatgaccctg gggtcggtct ggccaagtca acctcgatgc aaccaaggta   21180
tcgtagcttc gatccggagg gatgatgatc ccatgaagtt tctcaaggac ccggttgtcg   21240
tagtttagga tgttatgccc gaccacgaac tttgcatggg cgatgatgcg gtagaacacg   21300
tccatttcct cgggccggaa tccccggact accccagtcg gaatgtctac tgcaacagcg   21360
caccatagcc tcgtgacctc attgaagagt ccgtccccct caaggtcata gatcacgtaa   21420
tcaaattggg gtgtcatcgt cagcaggtac ctcgtcgtaa ctgccctcac gctcaaccaa   21480
gcgacccgtc tcagggttat acttggtgaa cactaggcca gtgttaccgt agttcctgtc   21540
cttgattaca cggatccgac tctcgtgctt ctcttcaccg tcagcctgct tgttccgctc   21600
gaagccgatc ataagctgac accaccgctg catagctcgg gaaccagtga actggctttc   21660
ctttacttca gcgccctcct cgtgggtacg gttaccttg ggtgggttaa ggtgggagaa    21720
gatgaagatc cgcagtccta gctcgtcggc catccctgcg agttctgtac agatacgggc   21780
tatctccgtg ttcatttcag aaggactaag gtggttggtc atggcggtca tgttatccag   21840
aaggatagtc ttcacatcca tggctacagc ccagaagcga atacactcct tgatatgatc   21900
ccaatcgttc tgaccccttgt tcttccacat gaagagtttg ccacggagtt tacccgcagc   21960
atctttaaag gcttgctcat cccactcgat atcggtcgg tggaagggca cgttggctac    22020
cttccccgcg atattcttaa gtgtcatggc tacctgctcc tccaagagga aggtccctac   22080
gttctccccg tgctcaatgc aattccaggc agcaatctcg tgggccaaca gggtcttacc   22140
gataccagta ccaccgccta ccccgatgat ttcaccatcc cgctgaccat aggttaggtt   22200
ggttaaacct tcccacgggt aactcttgcc ccacttgggg ggttccagag cctcagcgta   22260
```

-continued

```
tacctcatcg acagtaacgg aacagtccgg agacttgacc ttgctgccga atcggatcat   22320
ctggtaaacc tcatcccccc ggttacgcat aagcatgtca ttagcgtcct tcagaggaag   22380
ctcgacaaac ttacactcgg ggtacagggc acgtaccttt tctactgact tacggccttc   22440
gtcgtccgca tcgtggcaat agatgacctc gttgaaccgc tcaaggacac cagactcctt   22500
aaggaatgca atgtcccgtc cagcagaacc aacacccgag gaccaactaa tggatgcctg   22560
ccgaagatgc ttccacttct cgggcagctt cgactccatg atctgggcca cagacatagc   22620
cgacagttca tcctcgcaga tgactaaccg caggtgtccc atatccttat gccgaagggt   22680
attatacccg aaggggtcta caccgcccct ggggcttcca cggtagtaga aagctttggg   22740
ttctaggatt cggacgttga acgctcggta ctcccttcg cgagtgcgtg atagtaatg    22800
ctcgataacg tcctcaccat tttcttgtga tagaccaaca cgtacccgt accgttcagc   22860
gattgatttg ctgatctttc gagtatcgag ggctttagtt ggatactcaa ggacttcgtt   22920
gacttcatgg atgatatcct cttcagattt ctccctccgc tctggtacct tgaaaccctc   22980
ttcgaggact tcgtagtgac cacaacggtt gcaacttccg aaccgagtac ccttttctgt   23040
atcaacgaac aagatgaggt gatttcctgt tttatcccca cctttagctc ggcaacccgg   23100
acaagccgta tcaccgatga ttttcttcac ttacccctcc agttgactct tgagaaccag   23160
gcttggtaca gcattcacgt tgcccggtag ggttttatag ggagttgtta cgaaggtacc   23220
gtagacttcc tccagttccc gaagacgatc ctcgattttc ttcaatcgct cccacatgaa   23280
gcgaatgcca atggattcgt cacagtaccc accgtagctg gtctcgggac tgtccgaggc   23340
ctccggaatc ttggagacct cgatggagtc ttggaggtgt cgctgggaag ctacaaggcc   23400
caggatctcc ttgaggagca tcttctgggc atgtagctct tggtgtccga aggtgttcgg   23460
ggtgtcgcgg tagacttcta ctgctttgtc tacggtcatt tcgttcatta tactgctcct   23520
tgtcgttttg ccaggtgtgc cttccagtcg ccatcttgga cgatatccat cgccatgtgg   23580
ctatcctgat ggtacaccag ggccttgatg cgttccccat tgattcggaa atccttgagg   23640
gtacgatcat accaacccgg ataaccctct agggcatcca ggttctccag catttcatcc   23700
cccgcttcgc cctcggggag ttgccagatt tcacctacga tgagatcagc acggaggcg    23760
aaggagagga tggggaagcc gccagcggag tacatcagac cccgctcgca ggatacagca   23820
ttgccgatga actcggcccc ttccagaagg tagtggttgt acaaacctga caggagagta   23880
ccataaacga aaacacgaac agccattaga tagtctcctc gaagattttg ctgaagccct   23940
tgacgtatgc ctccagggcg ctgccttcag cgtccagacc tggggcggtg ttgatctcca   24000
ggacaaaggc ccggccagtg gcgtgctgga agatgatatc tactgcaccg aagtccagcc   24060
cagccacctg gattgcctct gccgctgccg acatagcctg ctcagcacca tcacggtcca   24120
ttgcatcgtt aaccccgtag acccagccgc cagctacgtt acgaacgatg ctttgtcctt   24180
cgttggtcac catttcattg gcaacacggc ggagtttgac ttggagaagt actacttccc   24240
cacggatcat atgggctcga aactcggtac gcttaccgac gattccctgg gtgaacagtt   24300
gtgccctggt gataacatcc gggatgtggg tgtgaccgta gatgtgtacc gggtagtggc   24360
cctgtctacg gagagcatcg atcgcagcaa cttctgcatc attgacagta cacaccaggt   24420
gaatgccgcg accgctatgg ccgttcagat cggtacgtgc atacatgcga ccagagatat   24480
tgagtacacc caaggcatct tcccaacgct cggtccaacg gggaatcagg tgaggggcat   24540
tggcctcgaa gtggcggaag aactccagct tgttagcagc gcggtaaaca actgccgggt   24600
cgttgaggaa cacaggggca atatcccgga gtcggtgagc ctctgcacca acggtacccc   24660
```

```
agttgattac cgcagtaccc gcacgacctc gataggtaga cccctcggag cgaaggattc   24720
gagcacccag ggcgttacga agagcgacag caccagcaga ggggcgggca cctttataga   24780
tatagaacat ggcaaatctc ctgtttctgt tgatggtagt gaagccagca atagcccctg   24840
gaatcctaag ttagatccca tgtacgcatc ttaggaaccg gcatgggtcg gccagggct   24900 attactaacg cactaccttaa ctcgaagtag tcttcgaaga gtcggtcgat agcttccgca   24960
atgactaccg gggccggtac caggaattcc tcgtccgggt tggcatcatt gagttcctgc   25020
tccttgactc gacgaatcga ctggatcttg tccagggtgt cacgggagaa gggatactta   25080 cggggttgcgt cggtctccat ctggatcact acttgacgct tcatcgttac ttgggtcatt   25140
ttgacctcct atttattttc gattacacac tcaccacaga tgaactcgca ctcatccagg   25200
ctaccagtga acttggcacc ttcgtatacc gtcagatgac gattacgctg gtcatatgcg   25260
gttgggatct tcccgcaaga tgcacatccc tgggacacga agtcccgaaa gacatgcacg   25320
ttgttgaagg tgtggccttg caccttcagg gggtaggtga tgttggccgg aggggtgttc   25380
cccgaggtgc cgccgacttg aaccctgggt ttagaatggg atttcgtctc cgatgagatc   25440
gttccaatcc tcaacactgg ggtagtctcc ccaggagtcg gccgatgctt tgggtccagg   25500
cagcttaccg ccagatcctc gacagtaacc ttgagatcac ggtcttggcc gacgaagtag   25560
gcattggaga tactccctcg gaggacggtg tatccgtgga cttttggcgac gttgatgcca   25620 tgagcttcga tgagaaggtt ttcttcacgc tcgattccag tgacagttcc gtactcgctg   25680
ccgtttgcgt aggcctcgat cttgacaaca tcgaaggtga cgagttgccg gtgcttgaag   25740
gtgctacctg ctgcgtcgag gttgttgttg atccggaggg tgttccttgc gtacgcatcg   25800
ccagacgttc catacgacga gcccgcttgg ctgcctttcg ttcccgcttg gctgccttgg   25860
cttcggctgt agtcatcgta gtccgagaca ccgacgtagc gactccacca tgccgctgct   25920
tgcctttcgc tttcgggaat cgggaggtcc agaaacgtga ccggagtggt ctgggggttct   25980 gcaccctttc gcactccggc ctccgtgaac gggatagtta ccaggacttc ggccttcagt   26040
tcagcgatgg gagaacgcag gcggatctta gcattgggtc gctccaggaa aaccttgagc   26100
atcccaggct ccgatgccca tacgatggtc ccggtggtgg taaccgccat gaacagagga   26160
cgatcttcgt tacggatgaa gttcaggcta cgttccttgg agtcccacca gacaaccgca   26220
gcagcaccag agaacttctc ctcgaacgtc ttccttggcac cgtggttggc aatggtagcg   26280
cacagcatgt tggagtccac gttgtactta tcattgccgt ccagcaggtg cagtccccag   26340
gtatccacgg tgccgttatg taccatggtg atgtggtcta cctggaaggg gtgggcattc   26400
ccatggtccg tcttgtcgcc catcgtggcg taacggttgt gacccatgta gatgcgagcc   26460
cgacccttgt ccaggaactc cttggtttca ggatcagcca ggaagtcgta ggcatctact   26520
gcccgcttgt gaattcctac ctcgttctta accgggtcga tcttggccaa accggtggcg   26580
tgagcaccac ggataatatc cacggccagg agggatttga aagagcgat ttcgttatca   26640 ctcgcgttag ttgtggcaca gaagcctacc aatccacaca ttgtatttct ccttagtaca   26700
tatctggttc gattgttacg ccggtatggc gctgaaggtg ctgcgggtta tccatgagca   26760
gtacgaaggc atcttgaaga gcctcttggt cctccagaag gtctcgtaca cgcacttggt   26820
gaccaatacg acgcagagaa gttaccgcag taatcgccgt atccagtcga acctgggtac   26880
ctgggaccat tgccaagttg taccgctctg ctgcaccatc gagtagtctg gaggtagtag   26940
atcgagccag cagcagccta cgatccaaaa ccctctgacg ctcacgttcc tgctcccgga   27000
```

```
gacgtcgctg acggttctgt tcatcctcca gaggatctac cccggagcga acaaagccca   27060
tggttgccac cgcgagagta gcactggcga tccccatttc acgaccaccc ggagacattt   27120
catagtccgg agatacccccc aggaagaaca catcacggag attcacctcg agagcacct   27180
tgaggaactc ttccaggggg gtttctgcgt gagccatggc gaaggccttg agacacaaca   27240
tacgctgcat caggcctacc atttcctgtc gagtagtcag ggcgtgagca ccacggaact   27300
cgatggaccc gaagttgtgg gttacctgga ggttcaaggc cgaatacttg gccaggagg   27360
taagacccaa gactttctct cggtcacctt ccggggccag gatacggcga ccgaaggtct   27420
gggccaacca gtcgttgctg aagaacggga tgcagaagtt actatcccga cgatacggct   27480
ggcagtgatc gaagaaaaca tcctcgaatg ccatgtaagt caggaccgtt cgttcgtaca   27540
ccggccactc tacgtcccgc atatccatgt gcaggtgggt ggagcaacgg aaggtaggag   27600
ccggagggt ttcttccatc gaacttacaa aggattcaac ccgagtgatt gccctctggc   27660
cagaggcggg accggagaag acatactcca taccctcccg cagagagccg tcacccttca   27720
gatcccaccc atccacttct ggccagttgt tgaggcttc cagttcgact tcgaacccga   27780
aggaagcaac cgcaggaagt tcctcgtggt gttccggggc gatgatctgg ttcttacgga   27840
accctatctg tgtgccaata actgacatag caagtcctcc tggttcttga attgttcatc   27900
tgcggacagc cgcccatcca ccatctggcc aaccttcact cccttccagt gtacaacccc   27960
atccttgatg aagaagtccc ggtgggaggg agcagagatc atttcctcgg cctgggtgaa   28020
gattcggatc atcatttcgc cggtgatagc ctgttggcca tgattcagca agatgttccg   28080
gggatctaca cccttgcgct gggtacggtt gttcacgagg aaggatacat aggtatcacg   28140
aaccccacga ccaaagacgt catagtaccc actggagggc cgcacgcttt ctacctcgct   28200
gtagacaacc cctccgtagt agttactgcc gtcggggcga tacacgttgc caaggagacg   28260
aaacccgtcg aattgacggt cgtcaccaat ggactcggta tcgtccacgt acactacccg   28320
aggctcgccg tccacccgga agaaggcata gtgggaggag tagtacatgt tgaagtctcc   28380
ggacaaccga tggcgattat tcaggtcatt catataccac ccccagcgct ttaagtgcag   28440
ctaccgccgc ggcgccgtcg ttctcgttga tgattcgctg gacttcatcg ccagatacga   28500
tggacttgta ctcctccagg aggtgcttgg aggtgtaagc ccgtactgcc atttcataga   28560
cccactcggt caggtctaca gagaagatcc agaagttcga caggctacgg tactcgcctc   28620
cgtaaggctt atagcgcatt gcgccagcct tgccgtacag cttcttacgc tgggtgtcac   28680
cgtcgaggat gacagaggcc aggcccagga ggtagtcaca catctgcatg acttctcggg   28740
tgttcgcctt ggtgactcgc tcgatgtggc tgaagccgat atggacgtgg ccgccagcag   28800
tgcgcagggt cggaggggca tccttcggca tcacgttctg acgacgagtc cagcagttgt   28860
agtccggctc gcaaccgaag acgtaagcct ggggaccgaa gctgcggagg agttcctcgt   28920
cgtacaggtg agaggacagg ttctcgatga tgttcatgcc gaaggggtgg agcatctggg   28980
cacccaggag tcgaacggaa acgatacgct tcacgaactc ttccttggtg ctggccgggt   29040
cgatgttgta ctccagaaga acgttgtctt cctggacggc accaccggct acagccaagg   29100
gggcttcctt ggttccaccg atgaagccga tgacgctctg ggggttacgg tcgtagccga   29160
cgaaaacttc gggatctgca ccgatcaggg ggattgcgtt gttcattgca tagtctccag   29220
tttttcgagg atttcgggga tgctgtaggg actggtgggt acggtctcag acctttcccg   29280
acctgggtca cctacgtcga tagtgatagg tgccatgatg gagaggatcc gatcattgtg   29340
tacaccttcg agcccgtcgc attcgatcag gtaatcgtcc ttggtatacc cttgccacaa   29400
```

```
ctcagcgtcg tgatgcttga gcttgtcctt gaactcttcg cgagtccgcc catgdatgct    29460
cttgatatcg aagtaggtga tctccttgta cccacctacg ataccatcca tgacttcgct    29520
gatgtagctg tcatccactt cccatccgtg actctcgcat ccttcccggt attcaccagc    29580
agtcaccggg aacatggcag gatagctgtc gcaatgggca gtgctaccta cctgggcaca    29640
agccgcgagg gtgaggatct ctgcattgca gcccaggatc ttatcacgat tttcctgggt    29700
gatgcgacgc atgaatcac ctacgcacca cagacgatcg cccattcgga gggcacagat     29760
gatggccgat gcgttcttcc tgaggtccac ccgtacatac actgcctgcc ggcgtcctgg    29820
gggagagaag tggtcgggat cattgagatt cttgagatca tcattgtaat cccaccaacg    29880
agtaggccag tcgatagagg ccgagaggat accaccgtcg gtaatcctgt tgaccaaatc    29940
actgttaagg aactccacca gtttaccaga ggtattctcg tgggtagata ccagcaggtg    30000
gccaaccccg gtaacccact cacctctgat accgccgtag gtctggtcgc aataggcccc    30060
gaagcaattt gtatattcgg ccatcatctt gaccgagtag tggtgtacca cagacccttc    30120
ggcgtcatag tacacattat gggctgcata cattcccatt tgatttctcc ttggttgtca    30180
gaagtttttc tcgatgaagc cttcgagggc cagtgagata tcccttatgc cgcttcgcca    30240
gccaatatca cccatgatcc ccagcatgac tactccgtat ttttcacagg taggatgaga    30300
aaggcggatg aaaccccccca gctcactatc tacggtcgtg tagggatctt tctttccgaa    30360
gacggttggc tgaggggcta tggtaaccac ctccaccttg tccaactgaa tcttcaggaa    30420
ttcagaccgc cagggtgtac tccttaccca ctcacgtcca cctggggcat cccgattggc    30480
catccaacga ccgaatcgca tagactcttc agcggattgg atgtggatat ccccccttctt   30540 gagatcatcc caatcgctac tgaacatgta gttagagagg ggatacccgg tgtagccatt    30600
ggctatcagc ccgtggaagg acattgcgag gtaggacttc cagaagccat acttctcagc    30660
aagcttcaga tggacctcct cctcacgacc tagatagtcg agtccgctgg atatcatctt    30720
gaagaggaac ttcatgatgg ggtaccagga atccagggtg tgtaccttgg ggttgaagta    30780
gataccgcag acaccttcct ttccgtgatg ggtgggggaa atcatttccg tcccgttaga    30840
atacttctcg aaggggggaat ccttggcctt gctttcgtaa gaccagaagt gaaccttcgg   30900
gatcttgaag gccttgccgc cgatggtgat ggtcttgagt tcaccttggg tacacttgtt    30960
gagtacatcg atgaacctct tgcttcggcg ggagcagatg aaggtccaac cgtcgagctt    31020
atagccgtgg gttaccggac cttccattgt accgaagcag gaggaagagg tcattacctt    31080 gagggctttta tcctctccat tcttggactt cataccgaag gcgtacttga tacgtgccat    31140 ttgtttctc cttggttgag ttagccagca ataccccccag dacaggaata ctaggggtat    31200
tactagcgac ctctaagtta cttagaaggc gccacgcgc tgttgcttgc ctttggtcgg     31260
tgccgacacc ttggtggcct tgaggttgcc gttcagggtc aattcaccgt tggagcagag    31320
acgctcgtag aaaaccttac gcttacccat tgttcacctc cttagcgaac gttgatgaaa    31380
ggcattgctt ggccgccggt gacgtaggta ggcagcttgc cgtcccactt ctcgatggca    31440
ttcagttcta ccacgccggg gttctggcgg agggcttcac cctggatgcg gaggctttcg    31500
gccttacctt gtgccaccag gatagccgct tgcttctcac cctcggctgc cgcgatagcc    31560
ttagctgcct cggcctgggt ctgacgaagt tcgttctcgc gctgcatcgc cgtctgagtg    31620
gccttgatct tggcattgat cgcctcgacc acctgcgccg gcaggccgat cataccgttg    31680
aggtacaggc tttcgacgat gatgccacgg gtggagaagt gctcacggac ggcagcttcg    31740
```

```
acttccttca cgaaggcttc cttgcccgga ccatagatgg cctcggcgga cttcttactg    31800
ctggcgttgt tcacggcgtt acggaccacc tgcggcacgt tcacgcttac gatctcgttc    31860
atgcccttgc ggtaggtctg aacagcagg ggtgcgctac ccggagcagc ccggagggtg    31920
acgccgatgg ggaagtccag cttcaggccg tccttgtcct gggcagtaac caccgccaga    31980
tcgaagttct ggttgaaggt ggggaacttg aacaattcct cgttggggt caggaacttc     32040 cagccgaccg gggtttcctt cagatcgacg cccttggagt cgcccatcat gttgacgacg    32100
acgccggtat agccagcggg aaccttggag caacctgcgg tgattgcgag ggcagcaatg    32160
gccaggaggc cgaggatttt cttcataggg attccttact tgtagagaag aggggtgatg    32220
tagaccatgc acaatgcgat gaacatgacg aacatcagta catagaagcc ccaatcatgc    32280
gggggcttac ctgggtggcc cagcaggccg tctatcttat gtatgttgtc gtagaggtcg    32340
gaggtatctt ctccgatgcc ctctaaatcc ttttggattg cctcacgag gcggcctcgc     32400 atctgttccg tcatagtaca tcagacctcc acccgtttac ctgagagctt cttggagtag    32460
gaagccatgt ggctagcaac ccagagggag tacaggatgg aaaggaccag gaggccggca    32520
cccatggcgt ttaccatggt gttagccggg acagcatct ggggtactac ccagaggatg     32580
cttatccatg cggggatagc caggagcatt acccgagtgt agagcttgag gaccattgtt    32640
cttacctctt tcttaagatg aagaagatag taggttagaa ccttaggtat cctagggata    32700
taaagcaacc ccggacacct taaggttatt ataccatact tccagcagaa tgtcaaggcc    32760
tagatgttac agacctttac agagcttgtc gaggtactcc gagtgctcga cggtaccggg    32820
gtagtcctgc aaaccaccga ggtgacgacg gagaacccca tggttgatga ggatttctgc    32880
cgcagccttc acgttgatga cgtggacccg gaccttggtc gagtggttgt cgctggatgc    32940
ccaggggttg tagtggcttc ccatgcggcg gaggatggtg tcggctacca cctgctcgct    33000
gttcaccgtg aagaccatcg taccgtggcc ctcgttggat tcacgacgga tagcgccgat    33060
cagttccttg gcgaaaccac gggggctgaa cccgttggat gcgaggccgg cgtaatggtc    33120
agcggtaccc gagggtccca tgccgatgta gattttgcg gtacagcagg agggaaagtc     33180
tctgcggtgc attagtaatc tcctttgatt agtcgtttgg ttgacttgat gattgaaacc    33240
aagggttgat agataacaac cacgaggcac atgtacggaa gggatactgg ccacaaggct    33300
cccaggatgt tgagatatc cctttccttc tggctcaact cacctgagtg cgagtcgcaa     33360
acagcaagac cgacgatacc agctacgagt agtgctatcg ccatgtagat caggaggaac    33420
acgatgaaca ggagtatgta gatcatggct tcatcactcc gtcaatgcca gcgccacaag    33480
cactgacaca acaaagaaga ccaggggag tccgatgatg aacaggaaca gagaggtcat     33540
ggtttcatta ccctcctctt aacatcacca cagattttac actgtaggtc gtaatagaca    33600
gattcgccta ccacccgacc tttgtgcatg aagtcgaagg gaccagtcct gatgatcttg    33660
taatcgtgga ccccgaagaa gcaccccagc cgaccgaaga ccatcaccaa tccctcgcgc    33720
agttgcaaca acgaccctct ttgggaccga agactggaat gcagtggggg caaggctccc    33780
cggattggat catagcctcc ctggcgtggc gcaggtaagc cgatcggctg gactccatac    33840
ctacggcagc caaggtgaaa ccaagctcac cacggggctc ctgggggcct tcctggaggc    33900
tcatgttgaa ccccgctttt tctacacgac gcttcatgcg gcgctcctgg gccattatct    33960
ggccgatcat gggtttattc ttcatacggc ccccacatac aggaattcac cgacaaccat    34020
ttggccggga atagctcaag gtgagtaccg atttccttgc acttgaggat gttgaagcca    34080
tccttgtgga tgatggtaac gagttcgccc ttcttgaggt aaaccaggtc gccagacccg    34140
```

```
gaatcacccg aatggacgta ggcaccatcc gccatctggc tgatgtggaa ttcaacccct     34200
ggctttgcta cagacacgct gaaagaagta ttggtcatgg cgtcaccta ctgaacccga     34260 tgaacgatgt ggtccaccgg gatgccgagt tcgaagaagg tttcggtgat gaactgcccg     34320
aaattgatga cctttacgtg gcgctcaccg tccttgctta ccaaccagaa aacctggggt     34380
ttagtggagt tcatagacga tacctacacg tttgccgaag atagatacac ggatgtgggt     34440
cacgtaccaa ccagggtacg ccttggggtt aggctggaac ctgcggatgc tgaccaagga     34500
ttccaaccag aggaacagat acagggcggg cgtcatagta cactagaccc tcacggtcat     34560
ttgagcgtcc accgggatga cctcgcagtc gctatggatg ctgcaaatga taccagcctc     34620
caggcaaacg aagtaaacat caccgtcatt ggggaggtag tggttgtggt catcccgaag     34680
gaccatccca tggatgttct caacacggaa aacatctgta gccttgaggg tatgcgccgg     34740
aaccttcttg ggcttttcta ccacattaat cttcatcgga ttacctcacg atgcaaaagg     34800
gatgctgtcc aaggtcgagg acaggacgaa gagaaccacc cacactacca gcaacaaccc     34860
attggaacgt gagcgtatgg cggcacatgc aatatacttc catgccatca ccgcgccctg     34920
ttcttaacca aagatgcccg cttggcacgg agcttgttca actccagggt tttaccaagg     34980
tggctaccat tggtattggt aagctcacga gttaccttgg caatcttgcg gtcgatggcc     35040
tcgatggctt gcatgttgcg gcttaccta cgatagtcgt tgcgtttcac gggatagttt     35100
cctttgttga tttcccaaga ctccccagcc tgcgaccata ggtccggtgg gggtttcggc     35160
caggaatcac catggcctca tcagttgggt cagttgatac ccatctcttc cttccagtcg     35220
cggaagaaga agtatccgat gcctacacaa gacaccacga tagctatcgt catcgcttca     35280
acctcttaat caattcttgc tgttcttgct tccaccgggg atcgggatgg accctcagca     35340
tcctagtgag cttctgcaac cgattaacca tcagtgccct ttcgtgggcg gcttcgtagg     35400
gggacttcat ttggtccacc cgcagaggcc catgcaacgg ccttccacat agacaccaca     35460
ggcgaactta ccatcgacga aagcccaacg gtaaaccacc tgttcaaccc cattgctatt     35520
gtacgaacgg gagttacaac gacctctcac gtaatcgttt gtaacagcta ccagaaagct     35580
accaaaaggg gtccacacgg ttttatcctc ggttagttca tccatacaat acacggacct     35640
accatgtact ctaggagga accaagggc gcgtcacagt acgcccctgg ccctgtccgt     35700
taggccgcct tcgtaggctc ttcgaacttc agcgccttga tctgtacgat acactcgtcg     35760
tgctcttcca gttggccctt gtcgatggcg cgttggatct tggcacggaa ggcagcgatg     35820
gccgcgtcga gggagaactc gtcggcaacg tcacgttcct tgcggtatcc gaaccacggc     35880
ttttcggtgg cacgctccag gttagtagcc ttgctgccgt cgtacacgaa ggggaactcg     35940
gccgacttgt tcttgtccga ctgagccttg atcttgccgt gatcgatgaa ccacgaggcc     36000
agagcgttgc ggcgggagcc cttgggcatg ccttgaaca gcttgcatgc caacgagact     36060
tcaccatgct cgtcgatgtg cttgagaatg tccaggccgg tagtttgaat cagcttgtcc     36120
agggatgcac cacgctgggc gatggtcttg atgatcccat tgatacgctt gtagtcgctc     36180
atagcttata cctctggttt gatgtgggtg acaggggagt tcttgcactt gctaggcttg     36240
taccaattgc gtagcttagt gtcctcgcgg ttacgccaat cggtattcat cagagccttt     36300
cgcttgcgtg ctccagcctt ttcctgaagg gaaacatact tgctgtccag gatcttgtta     36360
caattggaaa tgatcccgaa cttctgttct gcccgctgct gagctttgcc aaggtgccca     36420
atgttaatac cttgagcacg agccttgcgg ctagccttgc ggcgcagctt cttatcgata     36480
```

```
gcagcgttca tcgtttcatc cttttggaat catcagccgg gacacgcatc ccgatacgat    36540
aaaggggtta gtcggcaaac cttggcattg gcgtagccgg cccctttccg cgttagtatc    36600
gctgttatgg tctgtcctct ggctatcctc gggggtcttc gtgtctactc gcccctacct    36660
tcgccagtat ctaccaagct tcgccctctg cgctaagcca ttgatactaa cccaacatac    36720
tgcccatcac gattccacca tgggctctgc taattgttta cgctggagca ggcaaccagt    36780
cggatagaca taaggcggcg tctatcaaag ccagcgctct aaaggagtat gcgctattcc    36840
ctcagctttc gggtttctcc cctgttcagt ccaaggaccg tcgagggtac actttcccca    36900
ggtggccgtc acctgatggg tgcccatgtt agagccttgg gcttggcttg tcaacccttt    36960
gacgggggtt agttcgtcca gttctctggc ataggctctt ttgctgagtg gccatcagtc    37020
ttgcttgtca aggctacgct aatccctaag gagtcatgca cgttatgccg ttgacgtggg    37080
gcgaactata ccgcttcacc gatcccttgt caaccccccga tacctgccgg ctttacactt    37140
gggcgacttg ggcgctcttc cctggttggc agccccccgga tagcactgcg gcaaggggga    37200
tggtggccga ggtagaacgt gggggccatt agacccggtt ccgcggggtt tgtcaagccc    37260 ctagggggttt cccccgatgc ctatcggttt ccctcaaggc ggagccatta ggccatattc    37320
tttacggggt tgtctactgg ttttcatac agtctaagga ctatcagtcc cccagcaaac    37380
ccccggatat gaacagtctt tgactaacat agggtatcaa cggaagtcaa taggggatca    37440
aggggttatc aagggatatt ccccggtct cccctggac tccctaaga tttttctta    37500 ggtctatccg atgaacggta tctctggggg ttgacccccg gactagcctt atggtatcct    37560
agggaggggc tagggctat acccctgggg ataggccacc cccactttat ctggggact    37620 cctgggggga tattccccag atacaccgga ggataaaata gacttttggg gtaaccccg    37680 gttataggcc ctggatcaaa gcacccttcg atacctgttg gtatattact ggataaaggg    37740
gcaataggcc aggacatagc aaacagaggt agtctagggg tatacctatg gaacaacctc    37800
agggagtacc tatagaacct ggatcaaggg aaccctatgc cacttacccc ttaccagcaa    37860
cctacgaagg gtagtcttag ggtatatcta tagaacccta tcataccgtt cgtcgggtaa    37920
atcatgtgat tatcaaagaa atatcaaaaa gtacttgaca aggtatccaa aatgtagtat    37980
aatagaccta taggctctta agattccttc ttccttttga cttacttact aagaaggtta    38040
gttaccttaa ggttatctta agatagtctt aagaaccact tccccattcc agcaaaaccc    38100
ctaacaaatc cgggtcttgc gactaaaaat aaaaagatg aaaagggct tgacaaaata    38160 gaaaagtgt gatataatag tattataagg ttgagaaatt agccttaatg gtgctttaga    38220
attcattggg atgtagctca gttggtagag cagggagctg ttaactctca ggtcgtaggt    38280
tcgagtccta ccgtcccagc cattatggcc cattaactca gcggttagag tgctcccctg    38340
tctagggaga agccgtcggt tcgaatccga catgggtcgc caacaaaggt cgttgtagag    38400
gtagatggct actaccatcc ggctgtaacc cggacgccat aggctagagg ttcaattcct    38460
tccttcgacc accattaact cctcgtagct cagttggtta gagtgcctgt cttggacaca    38520
ggaggtcgta ggttcgagtc ctaccggggt gaccatttag agagatcgga gcagtgtatg    38580
tcagacgaaa aggttgtctc gattgggct gctcctcttt ctgctaaaga aaagctagac    38640
ctctattgtg aggctctggc agatggtatg aacaaaaccc aagcatatat agccgctggg    38700
ttctctccta atcatgcgca acgcaacgta gctgcatacc atcgaaagca tgccgaatac    38760
atcaacgcct ttatctctga gcgcatcggg agtcatgtcc ctatgcgct tcgtgtggtt    38820 gtagagatcg ctagcaaccc agaagagaaa ggtgggattc gcctcaaggc ggcccaggat    38880
```

```
atcctggatc gtggaggctt cggagctaag cagaaactgg agcttactac taagaatgtg    38940
gaagatatgt ccgcagagga tctaatcagt gaagttcgac gaattctcga cgaagagcca    39000
gagttggcta aagtcatttc tttcccagcc tcttaagtac cttgatctaa tcaagcgaag    39060
agaggggttg gtactaaagt ggtacaaaga ctccctcggg aaagtaactg gtggttatgg    39120
ccacttgcaa ctccctgggg aagacggacc gattacccta gcacgagcag agacttggct    39180
agaaaaggat agtaaggcag cctatgatgc agcccaaggg caagtatctc agctgccttt    39240
ttgcactcca gagctattcg atgccctcgt tagcgtcaat ttccagctgg gtacagcgtg    39300
gacgaagaag ttccccaaga cgtggaatct tctgaaatcc ggaaggtttg atgaggctgc    39360
atgggaggca gaggatagcc tctgggctaa acaaactcca gtgcgcgtaa gggacctcca    39420
acgggccctg tggcgtgcat caacagtagg tgacaaggtg gtctaatgga tacccaagag    39480
cggctacgga atctagtcag ggagttggcg gagcggcaga agtatttccg catgaaccag    39540
tatactcctt atgggtggca agagaagttt atcgcagctt cctcgaactg cgcccagttg    39600
ctggctatga ctggtaaccg ctgtggtaaa acctacaccg gggcctttat catggcctgc    39660
cacctcaccg gtcgctaccc tgagtggtgg actggtagaa agtatgatcg tccagtgaac    39720
tgctgggcgg cggggatctc cacggatacc actcgggata ttcttcagtc cgaactacta    39780
ggtgactgga agaaccctga ggcttttgga acggggatga tccccaagga agatatcgta    39840
gagacgattc gtagggaagg taaacccgga tgtgtgcaag cagtagttgt taagcatgcc    39900
tccgggggcc tctcgtccct tatcttcaag tcctacgaaa tgtcccagga caaattcatg    39960
ggtactgcca tcgacgtcat ctggctcgat gaggaatgcc ccaaggatat ttatacccag    40020
tgtgtaaccc gaacggctac tactgggggt attgtatatc tgacgtttac cccagagcat    40080
ggtctgacgg agatcgtcaa ggacttcctc caggatctta aacctggtca gttccttgtc    40140
catgcaagct gggaagacgc tccacacctc agtccagaag ttaaagagca gctactctcg    40200
gtatactctc cagcagaacg caggatgagg gccgagggtg ttcctatgct cggatctggt    40260
gtagtcttcc ccattctgga agagaagttt gtatgtgagc ctttccagat cccgatcac     40320 ttccatagga tcatcggtat cgacctcggg tttgaccacc ctaacgctat cgcctgtgtg    40380
gcctgggacc ctgagaaaga caaatactac ctctatgatg agagaagtga gagtggtgag    40440
acccttggga tgcacgctga tgctatctac ctgaagggtg gtcaccagat cccggtagtt    40500
gtcccccacg atgcctttaa gcacgatgga gcaacctctg gtcgtagatt cgtagacctt    40560
cttaaagatg accacaacct caatgtagtg tatgagccct tcagtaaccc accgggtcct    40620
gatggtaaac acggaggtaa ctctgtagag ttcggtgtta actggatgtt gacccgtatg    40680
gagaatggtc atctgaaggt gtttaatacg tgtacgaact tcctaaaaga aatgaaaatg    40740
taccaccgaa aggacggaaa gattatcgac agaaacgacg atatgatatc cgctacccgg    40800
tatgccctgt tgatggcttc ccggcatgca cgtcctggtg ctgtacgaaa cagtggatac    40860
tacaggagtg atactgcaaa gttgacccct gattggtttg ggagtattgt ctaatggcta    40920
agcgtcgtcg caagattaag cctatggatg atgaacaggt acttcgtcat ctagaccaac    40980
ttgttaacga cgcccttgat ttcaactctt cggaactttc caagcagcgt tctgaggccc    41040
tgaagtatta cttcggtgag cccttcggta atgagcgccc tgggaagtcc gcgattgtat    41100
ctagggacgt ccaagagact gtagactgga ttatgccttc tcttatgaag gtattcacgt    41160
caggcggtca agtagttaag tatgaacctc agactgccga ggatgttgaa caggcagagc    41220
```

```
aagagactga atatgtgaac tacctcttca tgcgtaagaa cgaggggttc aaggtaatgt    41280
tcgattggtt ccaagacact ctgatgatga agaccggggt tgtaaaggtc tacgtggaag    41340
aggtcctgaa ccccaccttc gaacgattct ctggtctctc tgaggaaatg gtagcggata    41400
tcctggctga tccagacact gagattctag cacagagtgt ggacgaggat ggaacctaca    41460
gtattaaaat tcgcaaggac aagaagaagc gagagattaa agtcacctgt atcaagcctg    41520
agaacttcct ggttgatcgg ttggctacct gcattgatga tgcacgcttc ctctgtcacc    41580
gtgagaagta taccgtaagt gacctgaggc tcttgggtgt tcccgaggat gtactagatg    41640
agcttccata cgatgagtat gaattctctg atagtcagcc agaaaggttg gtacgtgata    41700
acttcgatat gactggccaa ctccagtaca actctgggga tgatgctgaa gccaaccgtg    41760
aggtatgggc ctccgagtgc tacacccttc tggacgtaga tggggatggt atctctgagt    41820
tgcgccgtat cctgtacgtg ggcgactaca tcatcagcaa cgagccttgg gattgccgtc    41880
ccttcgctga cctgaatgcc tatcgaattg cccataagtt ccacgggatg agtgtctacg    41940
ataagatccg agacattcaa gagatccgtt cggtgctcat gcgcaacatc atggacaata    42000
tctaccggac caaccagggg cgatctgtag tcctggatgg ccaggttaac ctcgaagact    42060
tgctgaccaa cgaggcagcg ggtatcgttc gggttaaggc catgaactct atcatgcctc    42120
tggagacccc tcagctgtct ggggaagtct acggtatgct agataggcta gaggctgata    42180
ggggtaagcg gacaggcatc actgatcgta cccgaggcct agaccaaaac accctacact    42240
ctaaccaagc ggctatgagt gttaaccagt tgatgactgc tgctgagcaa cagattgacc    42300
tgattgcccg gatgtttgca gagactggtg ttaagcgttt gttccaactt ctgcatgacc    42360
atgccatcaa gtaccagaat caggaagagg tcttccagct acgaggcaag tgggttgcta    42420
ttaaccctgc caactggcga gagagatccg acctgacggt taccgttggt attggtaaca    42480
tgaacaaaga ccagcagatg ctccacctta tgcgtatctg ggaaatggcc caggctgtag    42540 taggggggtgg tggtcttggg gtccttgtct ctgagcagaa cctttataat atccttaagg    42600
aagtcacaga gaacgctggg tacaaagacc cggatcgctt ctggactaac ccggattctc    42660
ctgaagctca acgggctaag gccatcagag agcagaagga agcacaacct aagcctgaag    42720
atatcaaagc ccaagctgat gcccaacgtg cccaatcgga cgctatggct aagcaagcgg    42780
aggcccagat gaagcaggta gaggctcaga tccgactggc tgagatcgaa ctgaagaagc    42840
aagaggctgt ccttcagcag agagaaatgg cccttaagga agcggaacta caacttgagc    42900
gtgatcgttt cacttgggaa cgggctcgta acgaagcgga gtatcatctt gaggcaactc    42960
aggctcgggc tgcttatatc ggagacggta aggtacctga gactaagaag ccctcgaagg    43020
cagtgaggaa ataatcttgg gagaacgttt tggctatagt ctagtgctga ctgatgcggc    43080
acaacagatg gtacgtgaga acgttcttcc tgagcttttc cgtattgtcc aagaagagat    43140
cgagggagag tggaagtcca cggcacctaa ggattcagaa tccagggagg ccatctacca    43200
cgaactacat gccctcaacc gcgtacaact tcgtattcag gctatcctgg attcgatcac    43260
tctaaaggag tataagtaat ggaccttgag aatcaaggca tggatgaatt cgaggcagcg    43320
gaagccttcg gagatttgct aggtgatgac ctcctggccc ccgtgatgaa accgtggatg    43380
gtaaagtcgt aggggaagaa gaggaggaag aggtagtaga cgaaggtact ccagaggaca    43440
ccgaagaggt tgagtccgag gaggaagaag agggttctga ggaagatccc gaggttgagt    43500
ccgaggaaga tcctgaggat aaactcttcg agatccgat tggggatgaa gtctacgagg    43560
ttaacttcga agagcttaag agtggctacc ttcgcaatga agagttcgta actcgacaag    43620
```

-continued

```
ctgaactaga ggatcagtat gcagctaagt tcgaagagct tgatgctgaa cgctctaatc  43680
tactggccga gcttgagcag tatgctgtta ccgctatcgc tggtgctaat cagtatgaca  43740
atgtaaactg ggagcagctt aaggcccagg atccagagaa gtatcaaacc cttcgactgg  43800
aagccctgga agcccgagac cgagcccagg ctcttatcaa acgtcgtaac gacattaagg  43860
ctatgcaaga gaagcgagcc gagattgtcc actctgccta cgttaagcgt cagacagagc  43920
tagccaagaa acttatcccg gaaatgacta cggatgagtc ttggggtgac aagattgtgt  43980
cctacggcaa atcgattgga tactccgagg atgagatccg agggatatct gatgcccgcc  44040
aactggctgt actcgatgca gcacgtaagt gggctgaatc tcaggtccgt cgcaaggctg  44100
ccctagagaa gaaggaggag actgaactac ctgctgctgt taagcctgta gctcgtaggg  44160
cggaagcctc agagggttct aagcgggtta aagctgcccg tgctaatctg aggaaagacc  44220
agtcggttga agccgctgct gctctcttct cctctctcga catttctaa tagaaggaag  44280
tacattatat ggcaactcca actaatgccg tctccactgt agagatcaac ggtaagcgcg  44340
aagaccttat cgatatcatc tacaacatcg caccctatga caccccgttc atgactgcta  44400
tcggcaaggg cgtagctacc gctatcaccc acgagtggca gactgatgaa ctccgccagc  44460
cgggtaagaa cacccgagtt gaaggtgagg atgcaaccat caaggctggt agcttcacca  44520
ccatgttgaa caactactgc caaatctcgg acgagaccct gcaagtcacc ggtaccgcag  44580
ataaggtcaa gaaggctggt cgtaagaacg aactggcgta tcagctggct aagaagtcga  44640
aggaactgaa gctggacatg gaatacgcca tggtcggtgc ccctcaggct aagatccagc  44700
gtaacaccac tactccgggt cagatggcaa atatctttgc ctactacaag accaacggtt  44760
cggtaggtgc taacggtacc ctgccaactg gtgatggttc cgacactggt accgctggtg  44820
acctccgtct tctgaccgaa gacatgctcc tgaatgcctc tgaggctatc tggcgcaacg  44880
gtggtcaggc taactcgatc cagacttcga gctcgatcaa gaaggccatc agcaagaaca  44940
tgaagggtcg tgcaactgag atcaccctgg acgcctcgga caaccgcatt gcgcagaccg  45000
tggacgtcta cgagagtgac ttcggtaagt acaccattcg tgccaaccgc tggttccacg  45060
aaaacaccat gttcatcttt gatccgaaga tgcacgccct ctgctacctg cgtccgttct  45120
tccagcatga actggctaag accggtgaca gcgagaagcg ccagctgctg gttgagtaca  45180
ccctgcgtgt aaacaacgag aagtccggtg ctc                              45213
```

PSEUDOMONAS AERUGINOSA BACTERIOPHAGE PSE-AEP-3 AND USE THEREOF FOR INHIBITING PROLIFERATION OF PSEUDOMONAS AERUGINOSA

CROSS-REFERENCE TO RELATED APPLICATIONS

This application is a U.S. National Phase Application of International Application No. PCT/KR2018/000507, filed Jan. 11, 2018, which claims priority to Korean Application No. 10-2017-0021315, filed Feb. 17, 2017, each of which are hereby incorporated by reference in their entirety.

The Sequence Listing submitted Aug. 16, 2019, as a text file named "08162_0057U1_Sequence_Listing.txt," created on Aug. 13, 2019, and having a size of 57,792 bytes is hereby incorporated by reference pursuant to 37 C.F.R. § 1.52(e)(5).

TECHNICAL FIELD

The present invention relates to a bacteriophage isolated from nature, which infects *Pseudomonas aeruginosa* to thus kill *Pseudomonas aeruginosa*, and a method of preventing or treating a *Pseudomonas aeruginosa* infection using a composition containing the same as an active ingredient. More particularly, the present invention relates to a *Podoviridae* bacteriophage Pse-AEP-3 (Accession number: KCTC 13165BP) isolated from nature, which has the ability to kill *Pseudomonas aeruginosa* and has the genome represented by SEQ ID NO: 1, and a method of preventing and treating a *Pseudomonas aeruginosa* infection using a composition containing the above bacteriophage as an active ingredient.

BACKGROUND ART

*Pseudomonas aeruginosa*, which is a gram-negative bacillus, is an opportunistic bacterium that is commonly found in natural environments but is capable of causing sepsis in people who have decreased immunity due to surgery, burns, trauma, or chemotherapy. *Pseudomonas aeruginosa* is a known major hospital infection pathogen and is a cause of various diseases such as endocarditis, pneumonia, meningitis and the like. In particular, *Pseudomonas aeruginosa* infection is frequently fatal in cystic fibrosis patients, and infants are known to experience serious loss of pulmonary function when infected with *Pseudomonas aeruginosa*.

Typically, vaccines and antibiotics are used for the prevention and treatment of infectious diseases caused by *Pseudomonas aeruginosa*. Here, the effectiveness of antibiotics has been continuously decreasing due to the proliferation of antibiotic-resistant bacteria. Hence, the development of drugs for use in the prevention or treatment of infection with antibiotic-resistant *Pseudomonas aeruginosa* is urgently required.

Recently, the use of bacteriophages as a countermeasure against bacterial diseases has attracted considerable attention. In particular, these bacteriophages are receiving great attention due to strong antibacterial activity against antibiotic-resistant bacteria. Bacteriophages are very small microorganisms infecting bacteria, and are usually simply called "phages". Once a bacteriophage infects a bacterium, the bacteriophage is proliferated inside the bacterial cell. After proliferation, the progeny of the bacteriophage destroy the bacterial cell wall and escape from the host bacteria, demonstrating that the bacteriophage has the ability to kill bacteria. The manner in which the bacteriophage infects bacteria is characterized by very high specificity thereof, and thus the range of types of bacteriophages infecting a specific bacterium is limited. That is, a certain bacteriophage may infect only a specific bacterium, suggesting that a certain bacteriophage is capable of providing an antibacterial effect only for a specific bacterium and thus is capable of killing the specific bacterium alone without harming other bacteria. Due to this bacteria specificity of bacteriophages, the bacteriophage confers antibacterial effects only upon target bacteria, but does not affect commensal bacteria in the environment or in the intestines of animals. Conventional antibiotics, which have been widely used for bacterial treatment, incidentally influence many other kinds of bacteria. This causes problems such as environmental pollution and the disturbance of normal flora in animals. In contrast, the use of bacteriophages does not disturb normal flora in animals, because the target bacterium is selectively killed. Hence, bacteriophages may be utilized safely, which thus greatly lessens the probability of adverse effects of use thereof compared to antibiotics.

Bacteriophages were first discovered by the English bacteriologist Twort in 1915 when he noticed that *Micrococcus* colonies softened and became transparent due to something unknown. In 1917, the French bacteriologist d'Herelle discovered that *Shigella dysenteriae* in the filtrate of dysentery patient feces was destroyed by something, and further studied this phenomenon. As a result, he independently identified bacteriophages, and named them bacteriophages, which means "eater of bacteria". Since then, bacteriophages acting against such pathogenic bacteria as *Shigella, Salmonella Typhi*, and *Vibrio cholerae* have been continually identified.

Owing to the unique ability of bacteriophages to kill bacteria, bacteriophages have attracted attention as a potentially effective countermeasure against bacterial infection since their discovery, and a lot of research related thereto has been conducted. However, since penicillin was discovered by Fleming, studies on bacteriophages have continued only in some Eastern European countries and the former Soviet Union, because the spread of antibiotics was generalized. Since 2000, the limitations of conventional antibiotics have become apparent due to the increase in antibiotic-resistant bacteria, and the possibility of developing bacteriophages as a substitute for conventional antibiotics has been highlighted, and thus bacteriophages are again attracting attention as antibacterial agents.

As demonstrated above, bacteriophages tend to be highly specific for particular bacteria. Because of this specificity, bacteriophages frequently exhibit an antibacterial effect only for certain strains of bacteria, even within the same species. In addition, the antibacterial strength of bacteriophages may vary depending on the target bacterial strain. Therefore, it is necessary to collect many kinds of bacteriophages that are useful in order to effectively control specific bacteria. Hence, in order to develop an effective bacteriophage utilization method for controlling *Pseudomonas aeruginosa*, many kinds of bacteriophages that exhibit antibacterial action against *Pseudomonas aeruginosa* must be acquired. Furthermore, the resulting bacteriophages need to be screened as to whether or not they are superior to others from the aspect of antibacterial strength and spectrum.

Disclosure

Technical Problem

Therefore, the present inventors endeavored to develop a composition applicable for the prevention or treatment of a Pseudomonas aeruginosa infection using a bacteriophage that is isolated from nature and is capable of killing Pseudomonas aeruginosa, and further to establish a method of preventing or treating a Pseudomonas aeruginosa infection using the composition. As a result, the present inventors isolated a bacteriophage suitable for this purpose from nature and determined the gene sequence of the genome, which distinguishes the isolated bacteriophage from other bacteriophages. Then, the present inventors developed a composition containing the bacteriophage as an active ingredient, and ascertained that this composition is capable of being used to effectively prevent or treat a Pseudomonas aeruginosa infection, thus culminating in the present invention.

Accordingly, it is an object of the present invention to provide a Podoviridae bacteriophage Pse-AEP-3 (Accession number: KCTC 13165BP) isolated from nature, which has the ability to kill Pseudomonas aeruginosa and has the genome represented by SEQ ID NO: 1.

It is another object of the present invention to provide a composition applicable for preventing a Pseudomonas aeruginosa infection, which contains, as an active ingredient, an isolated bacteriophage Pse-AEP-3 (Accession number: KCTC 13165BP) infecting Pseudomonas aeruginosa to thus kill Pseudomonas aeruginosa, and a method of preventing a Pseudomonas aeruginosa infection using the composition.

It is another object of the present invention to provide a composition applicable for treating a disease induced by Pseudomonas aeruginosa, which contains, as an active ingredient, the isolated bacteriophage Pse-AEP-3 (Accession number: KCTC 13165BP) infecting Pseudomonas aeruginosa to thus kill Pseudomonas aeruginosa, and a method of treating a disease induced by Pseudomonas aeruginosa using the composition.

It is another object of the present invention to provide a pharmaceutical composition for preventing or treating a Pseudomonas aeruginosa infection using the above-described composition, which contains, as an active ingredient, the isolated bacteriophage Pse-AEP-3 (Accession number: KCTC 13165BP) infecting Pseudomonas aeruginosa to thus kill Pseudomonas aeruginosa.

It is another object of the present invention to provide a disinfectant, which contains, as an active ingredient, the isolated bacteriophage Pse-AEP-3 (Accession number: KCTC 13165BP) infecting Pseudomonas aeruginosa to thus kill Pseudomonas aeruginosa. In particular, this disinfectant is effective at preventing infection in a hospital.

It is another object of the present invention to provide an antibiotic, which contains, as an active ingredient, the isolated bacteriophage Pse-AEP-3 (Accession number: KCTC 13165BP) infecting Pseudomonas aeruginosa to thus kill Pseudomonas aeruginosa.

Technical Solution

The present invention provides a Podoviridae bacteriophage Pse-AEP-3 (Accession number: KCTC 13165BP) isolated from nature, which has the ability to specifically kill Pseudomonas aeruginosa and has the genome represented by SEQ ID NO: 1, and a method of preventing or treating a Pseudomonas aeruginosa infection using a composition containing the same as an active ingredient.

The bacteriophage Pse-AEP-3 was isolated by the present inventors and then deposited at Korean Collection for Type Cultures, Korea Research Institute of Bioscience and Biotechnology on Nov. 29, 2016 (Accession number: KCTC 13165BP).

The present invention also provides a pharmaceutical composition applicable for the prevention or treatment of a Pseudomonas aeruginosa infection, which contains the bacteriophage Pse-AEP-3 as an active ingredient. Examples of the pharmaceutical composition include, but are not limited to, disinfectants or antibiotics.

Since the bacteriophage Pse-AEP-3 contained in the composition of the present invention kills Pseudomonas aeruginosa effectively, it is effective in the prevention (prevention of infection) or treatment (treatment of infection) of diseases, such as urinary tract infection, wound infection, bacteremia, endocarditis and the like, caused by Pseudomonas aeruginosa. Therefore, the composition of the present invention is capable of being utilized for the prevention and treatment of diseases caused by Pseudomonas aeruginosa. In the present invention, diseases caused by Pseudomonas aeruginosa may include urinary tract infections, wound infections, bacteremia, endocarditis, and the like.

Pseudomonas aeruginosa in this specification may be sensitive to existing antibiotics or may be resistant to existing antibiotics. Briefly, it does not matter whether or not resistance to existing antibiotics is exhibited.

As used herein, the terms "prevention" and "prevent" refer to (i) prevention of a Pseudomonas aeruginosa infection and (ii) inhibition of the development of diseases caused by a Pseudomonas aeruginosa infection.

As used herein, the terms "treatment" and "treat" refer to all actions that (i) suppress diseases caused by Pseudomonas aeruginosa and (ii) alleviate the pathological condition of the diseases caused by Pseudomonas aeruginosa.

As used herein, the terms "isolate", "isolating", and "isolated" refer to actions that isolate bacteriophages from nature by using diverse experimental techniques and that secure characteristics that can distinguish the bacteriophage of the present invention from others, and further include the action of proliferating the bacteriophage of the present invention using bioengineering techniques so that the bacteriophage is industrially applicable.

The pharmaceutically acceptable carrier included in the composition of the present invention is one that is generally used for the preparation of a pharmaceutical formulation, and examples thereof include lactose, dextrose, sucrose, sorbitol, mannitol, starch, acacia rubber, calcium phosphate, alginate, gelatin, calcium silicate, microcrystalline cellulose, polyvinyl pyrrolidone, cellulose, water, syrup, methylcellulose, methylhydroxybenzoate, propylhydroxybenzoate, talc, magnesium stearate, and mineral oil, but are not limited thereto. The composition of the present invention may additionally include lubricants, wetting agents, sweeteners, flavors, emulsifiers, suspension agents, and preservatives, in addition to the above ingredients.

The composition of the present invention may be used through application or spraying on a diseased site, or may be administered through oral administration or parenteral administration. Here, the parenteral administration may include intravenous administration, intraperitoneal administration, intramuscular administration, subcutaneous administration or local administration.

The appropriate application, spray and dose of the pharmaceutical composition of the present invention may vary depending on factors such as the formulation method, the mode of administration, the age, weight, gender and diseased condition of the subject animal or patient, diet, administration time, administration route, excretion rate, and responsiveness. Usually, a dose effective for the desired treatment may be easily determined and prescribed by skilled physicians or veterinarians.

The bacteriophage Pse-AEP-3 is contained as an active ingredient in the composition of the present invention. The bacteriophage Pse-AEP-3 is contained at a concentration of $1\times10^1$ pfu/ml to $1\times10^{30}$ pfu/ml or $1\times10^1$ pfu/g to $1\times10^{30}$ pfu/g, and preferably at a concentration of $1\times10^4$ pfu/ml to $1\times10^{15}$ pfu/ml or $1\times10^4$ pfu/g to $1\times10^{15}$ pfu/g.

The composition of the present invention may be formulated using a pharmaceutically acceptable carrier and/or excipient in accordance with a method that may be easily carried out by those skilled in the art to which the present invention belongs, in order to prepare the same in a unit dosage form or insert the same into a multi-dose container. Here, the formulation thereof may be provided in the form of a solution, a suspension, or an emulsion in an oil or aqueous medium, or in the form of an extract, a powder, a granule, a tablet, or a capsule, and may additionally contain a dispersant or a stabilizer.

The composition of the present invention may be prepared as a disinfectant or an antibiotic depending on the purpose of use thereof, without limitation thereto. As used herein, the term "antibiotic" collectively refers to preservatives, bactericides and antibacterial agents.

In order to improve the effectiveness thereof, bacteriophages that confer antibacterial activity against other bacterial species may be further included in the composition of the present invention. In addition, other kinds of bacteriophages that have antibacterial activity against *Pseudomonas aeruginosa* may be further included in the composition of the present invention. These bacteriophages may be combined appropriately so as to maximize the antibacterial effects thereof, because their antibacterial activities against *Pseudomonas aeruginosa* may vary from the aspects of antibacterial strength and spectrum.

Advantageous Effects

According to the present invention, the method of preventing or treating a *Pseudomonas aeruginosa* infection using the composition containing the bacteriophage Pse-AEP-3 as an active ingredient can have the advantage of very high specificity for *Pseudomonas aeruginosa*, compared to conventional methods based on existing antibiotics. This means that the composition can be used for preventing or treating a *Pseudomonas aeruginosa* infection without affecting other bacteria, namely useful commensal bacteria, and has fewer side effects attributable to the use thereof. Typically, when antibiotics are used, commensal bacteria are also damaged, thus entailing various side effects owing to the use thereof. Meanwhile, in the case of various bacteriophages exhibiting antibacterial activity against the same species of bacteria, the antibacterial activities of the bacteriophages are different with regard to antibacterial strength and spectrum [the spectrum of the antibacterial activity of the bacteriophages applied to individual bacteria strains in terms of the strains of various bacteria belonging to *Pseudomonas aeruginosa*, bacteriophages usually being effective only on some bacterial strains, even within the same species, and the antibacterial activity of bacteriophages thus depending on the bacterial strain even for the same species of bacteria]. Accordingly, the present invention can provide antibacterial activity against *Pseudomonas aeruginosa* different from that of other bacteriophages acting on *Pseudomonas aeruginosa*. This provides applicability to a great variety of industrial fields.

DESCRIPTION OF DRAWINGS

FIG. 1 is an electron micrograph showing the morphology of the bacteriophage Pse-AEP-3.

FIG. 2 is a photograph showing the results of an experiment on the ability of the bacteriophage Pse-AEP-3 to kill *Pseudomonas aeruginosa*, in which the clear zone is a plaque formed by lysis of the bacteria.

MODE FOR INVENTION

Hereinafter, the present invention will be described in more detail with reference to Examples. However, the Examples are merely examples of the present invention, and the scope of the present invention is not limited to the Examples.

Example 1: Isolation of Bacteriophage Capable of Killing *Pseudomonas aeruginosa*

Samples were collected from nature to isolate the bacteriophage capable of killing *Pseudomonas aeruginosa*. Here, the *Pseudomonas aeruginosa* used for the bacteriophage isolation had been previously isolated and identified as *Pseudomonas aeruginosa* by the present inventors.

The procedure for isolating the bacteriophage is described in detail hereinafter. The collected sample was added to a TSB (Tryptic Soy Broth) culture medium (casein digest, 17 g/L; soybean digest, 3 g/L; dextrose, 2.5 g/L; NaCl, 5 g/L; dipotassium phosphate, 2.5 g/L) inoculated with *Pseudomonas aeruginosa* at a ratio of 1/1000, followed by shaking culture at 37° C. for 3 to 4 hr. Upon completion of the culture, centrifugation was performed at 8,000 rpm for 20 min and a supernatant was recovered. The recovered supernatant was inoculated with *Pseudomonas aeruginosa* at a ratio of 1/1000, followed by shaking culture at 37° C. for 3 to 4 hr. When the sample contained the bacteriophage, the above procedure was repeated a total of 5 times in order to sufficiently increase the number (titer) of bacteriophages. After repeating the procedure 5 times, the culture broth was subjected to centrifugation at 8,000 rpm for 20 min. After centrifugation, the recovered supernatant was filtered using a 0.45 μm filter. The obtained filtrate was used in a typical spot assay for examining whether or not a bacteriophage capable of killing *Pseudomonas aeruginosa* was included therein.

The spot assay was performed as follows: TSB culture medium was inoculated with *Pseudomonas aeruginosa* at a ratio of 1/1000, followed by shaking culture at 37° C. overnight. 3 ml ($OD_{600}$ of 1.5) of the culture broth of *Pseudomonas aeruginosa* prepared above was spread on the culture medium (casein digest, 15 g/L; soybean digest, 5 g/L; NaCl, 5 g/L; agar, 15 g/L) of a TSA (Tryptic Soy Agar) plate. The spread plate was left on a clean bench for about 30 min to thus dry the spread solution. After drying, 10 μl of the prepared filtrate was spotted onto the plate culture medium on which *Pseudomonas aeruginosa* was spread and then left to dry for about 30 min. After drying, the plate culture medium that was subjected to spotting was cultured without shaking at 37° C. for one day, and then examined for the formation of clear zones at the positions where the filtrate was dropped. In the case in which the filtrate generated a clear zone, it was judged that the bacteriophage capable of killing *Pseudomonas aeruginosa* was included therein. Through the above examination, it was possible to obtain a filtrate containing the bacteriophage having the ability to kill *Pseudomonas aeruginosa*.

The pure bacteriophage was isolated from the filtrate confirmed above to have the bacteriophage capable of killing *Pseudomonas aeruginosa*. A conventional plaque assay was used to isolate the pure bacteriophage. In detail, a plaque formed in the course of the plaque assay was recovered using a sterilized tip, which was then added to the culture broth of *Pseudomonas aeruginosa*, followed by culturing at 37° C. for 4 to 5 hr. After the culturing, centrifugation was performed at 8,000 rpm for 20 min to obtain a supernatant. The *Pseudomonas aeruginosa* culture broth was added to the obtained supernatant at a volume ratio of 1/50, followed by culturing at 37° C. for 4 to 5 hr. In order to increase the number of bacteriophages, the above procedure was repeated at least 5 times. Then, centrifugation was performed at 8,000 rpm for 20 min in order to obtain the final supernatant. A plaque assay was further performed using the resulting supernatant. In general, the isolation of a pure bacteriophage is not completed through a single iteration of a procedure, so the above procedure was repeated using the resulting plaque formed above. After at least 5 repetitions of the procedure, the solution containing the pure bacteriophage was obtained. The procedure for isolating the pure bacteriophage was repeated in its entirety until the generated plaques became similar to each other with respect to size and morphology. In addition, final isolation of the pure bacteriophage was confirmed using electron microscopy. The above procedure was repeated until the isolation of the pure bacteriophage was confirmed using electron microscopy. The electron microscopy was performed according to a conventional method. Briefly, the solution containing the pure bacteriophage was loaded on a copper grid, followed by negative staining with 2% uranyl acetate and drying. The morphology thereof was then observed using a transmission electron microscope. The electron micrograph of the pure bacteriophage that was isolated is shown in FIG. 1. Based on the morphological characteristics thereof, the novel bacteriophage that was isolated above was confirmed to be a *Podoviridae* bacteriophage.

The solution containing the pure bacteriophage confirmed above was subjected to the following purification process. The *Pseudomonas aeruginosa* culture broth was added to the solution containing the pure bacteriophage at a volume ratio of 1/50 based on the total volume of the bacteriophage solution, followed by further culturing for 4 to 5 hr. After the culturing, centrifugation was performed at 8,000 rpm for 20 min to obtain a supernatant. This procedure was repeated a total of 5 times in order to obtain a solution containing a sufficient number of bacteriophages. The supernatant obtained from the final centrifugation was filtered using a 0.45 μm filter, followed by a conventional polyethylene glycol (PEG) precipitation process. Specifically, PEG and NaCl were added to 100 ml of the filtrate until reaching 10% PEG 8000/0.5 M NaCl, which was then left at 4° C. for 2 to 3 hr. Thereafter, centrifugation was performed at 8,000 rpm for 30 min to obtain the bacteriophage precipitate. The resulting bacteriophage precipitate was suspended in 5 ml of a buffer (10 mM Tris-HCl, 10 mM MgSO$_4$, 0.1% gelatin, pH 8.0). The resulting material may be referred to as a bacteriophage suspension or bacteriophage solution.

As a result, the pure bacteriophage purified above was collected, was named the bacteriophage Pse-AEP-3, and deposited at Korean Collection for Type Cultures, Korea Research Institute of Bioscience and Biotechnology on Nov. 29, 2016 (Accession number: KCTC 13165BP).

Example 2: Separation and Sequence Analysis of Genome of Bacteriophage Pse-AEP-3

The genome of the bacteriophage Pse-AEP-3 was separated as follows. The genome was separated from the bacteriophage suspension obtained using the same method as in Example 1. First, in order to eliminate DNA and RNA of *Pseudomonas aeruginosa* included in the suspension, 200 U of each of DNase I and RNase A was added to 10 ml of the bacteriophage suspension and then left at 37° C. for 30 min. After being left for 30 min, in order to stop the DNase I and RNase A activity, 500 μl of 0.5 M ethylenediaminetetraacetic acid (EDTA) was added thereto, and the resulting mixture was then left for 10 min. In addition, the resulting mixture was further left at 65° C. for 10 min, and 100 μl of proteinase K (20 mg/ml) was then added thereto so as to break the outer wall of the bacteriophage, followed by reaction at 37° C. for 20 min. Thereafter, 500 μl of 10% sodium dodecyl sulfate (SDS) was added thereto, followed by reaction at 65° C. for 1 hr. After reaction for 1 hr, 10 ml of the solution of phenol:chloroform:isoamyl alcohol, mixed at a component ratio of 25:24:1, was added to the reaction solution, followed by mixing thoroughly. In addition, the resulting mixture was subjected to centrifugation at 13,000 rpm for 15 min to thus separate layers. Among the separated layers, the upper layer was selected, and isopropyl alcohol was added thereto at a volume ratio of 1.5, followed by centrifugation at 13,000 rpm for 10 min in order to precipitate the genome. After the precipitate was recovered, 70% ethanol was added to the precipitate, followed by centrifugation at 13,000 rpm for 10 min to wash the precipitate. The washed precipitate was recovered, vacuum-dried and then dissolved in 100 μl of water. This procedure was repeated to thus obtain a large amount of the genome of the bacteriophage Pse-AEP-3.

Information on the sequence of the genome of the bacteriophage Pse-AEP-3 obtained above was secured by performing next-generation sequencing analysis using a Pacbio apparatus provided by the National Instrumentation Center for Environmental Management, Seoul National University. The finally analyzed genome of the bacteriophage Pse-AEP-3 had a size of 45,213 bp, and the whole genome sequence is represented by SEQ ID NO: 1.

The homology (similarity) of the bacteriophage Pse-AEP-3 genomic sequence obtained above with previously reported bacteriophage genomic sequences was investigated using BLAST on the web. Based on the results of the BLAST investigation, the genomic sequence of the bacteriophage Pse-AEP-3 was found to have relatively high homology with the sequence of the *Pseudomonas aeruginosa* bacteriophage PaP4 (GenBank Accession number: KC294142.1) (identity: 93%). However, the bacteriophage Pse-AEP-3 has a circular genome and *Pseudomonas aeruginosa* bacteriophage PaP4 has a linear genome, and thus there is a significant difference in the genomic topology therebetween, and the number of open reading frames (ORFs) on the bacteriophage Pse-AEP-3 genome is 69, whereas the *Pseudomonas aeruginosa* bacteriophage PaP4 has 70 open reading frames, unlike the bacteriophage Pse-AEP-3.

Therefore, it can be concluded that the bacteriophage Pse-AEP-3 is a novel bacteriophage different from conventionally reported bacteriophages. Moreover, since the antibacterial strength and spectrum of bacteriophages typically depend on the type of bacteriophage, it is considered that the bacteriophage Pse-AEP-3 can provide antibacterial activity different from that of any other bacteriophages reported previously.

Example 3: Investigation of Ability of Bacteriophage Pse-AEP-3 to Kill *Pseudomonas aeruginosa*

The ability of the isolated bacteriophage Pse-AEP-3 to kill *Pseudomonas aeruginosa* was investigated. In order to evaluate the killing ability, the formation of clear zones was observed using a spot assay in the same manner as described in connection with Example 1. A total of 10 strains, including 9 strains that had been isolated and identified as *Pseudomonas aeruginosa* by the present inventors and 1 strain (*Pseudomonas aeruginosa* ATCC 15692) procured from the American Type Culture Collection (ATCC), were used as *Pseudomonas aeruginosa* for the investigation of killing ability. The bacteriophage Pse-AEP-3 had the ability to kill a total of 9 strains, including 1 strain procured from ATCC, among 10 strains of *Pseudomonas aeruginosa*, that is, the experimental target. The representative experimental results thereof are shown in FIG. 2. Meanwhile, the ability of the bacteriophage Pse-AEP-3 to kill *Staphylococcus aureus, Pasteurella multocida, Clostridium perfringens, Lactobacillus plantarum, Streptococcus uberis* and *Enterococcus faecalis* was also measured. Consequently, the bacteriophage Pse-AEP-3 was found not to have the ability to kill these microorganisms.

Therefore, it can be concluded that the bacteriophage Pse-AEP-3 has high ability to kill *Pseudomonas aeruginosa* and an antibacterial effect against many *Pseudomonas aeruginosa* bacteria, indicating that the bacteriophage Pse-AEP-3 can be used as an active ingredient of the composition for preventing and treating *Pseudomonas aeruginosa* infection.

Example 4: Experiment for Prevention of *Pseudomonas aeruginosa* Infection Using Bacteriophage Pse-AEP-3

100 μl of a bacteriophage Pse-AEP-3 solution at a level of $1\times10^9$ pfu/ml was added to a tube containing 9 ml of a TSB culture medium. To another tube containing 9 ml of a TSB culture medium, only the same amount of TSB culture medium was further added. A *Pseudomonas aeruginosa* culture broth was then added to each tube so that absorbance reached about 0.5 at 600 nm. After addition of *Pseudomonas aeruginosa*, the tubes were placed in an incubator at 37° C., followed by shaking culture, during which the growth of *Pseudomonas aeruginosa* was observed. As shown in Table 1 below, it was observed that the growth of *Pseudomonas aeruginosa* was inhibited in the tube to which the bacteriophage Pse-AEP-3 solution was added, whereas the growth of *Pseudomonas aeruginosa* was not inhibited in the tube to which the bacteriophage solution was not added.

TABLE 1

Growth inhibition of *Pseudomonas aeruginosa*

| Classification | $OD_{600}$ absorbance value | | |
|---|---|---|---|
| | 0 min after culture | 60 min after culture | 120 min after culture |
| Not added with bacteriophage solution | 0.5 | 0.7 | 1.6 |
| Added with bacteriophage solution | 0.5 | 0.3 | 0.1 |

The above results show that the bacteriophage Pse-AEP-3 of the present invention not only inhibits the growth of *Pseudomonas aeruginosa* but also has the ability to kill *Pseudomonas aeruginosa*. Therefore, it is concluded that the bacteriophage Pse-AEP-3 can be used as an active ingredient of the composition for preventing a *Pseudomonas aeruginosa* infection.

Example 5: Treatment 1 of Infectious Disease Caused by *Pseudomonas aeruginosa* Using Bacteriophage Pse-AEP-3

The therapeutic effect of the bacteriophage Pse-AEP-3 on animals afflicted with *Pseudomonas aeruginosa* was evaluated. 2 groups of 40 2-day-old chicks per group were prepared and reared separately, and the experiment was performed for 14 days. For 3 days from the fifth day after the start of the experiment, a feed containing $1\times10^7$ cfu/g of *Pseudomonas aeruginosa* was supplied in a typical feeding manner. From the last day of feeding with feed containing *Pseudomonas aeruginosa, Pseudomonas aeruginosa* was found in the feces of both groups. From the next day (the eighth day after the start of the experiment) after the supply of the feed including *Pseudomonas aeruginosa* for 3 days, a feed containing $1\times10^8$ pfu/g of bacteriophage Pse-AEP-3 was fed to chicks in the experimental group (administered with bacteriophage) in a typical feeding manner. In contrast, a feed having the same composition but excluding bacteriophage Pse-AEP-3 was fed to chicks in the control group (not administered with bacteriophage) in the same manner. From the ninth day after the start of the experiment, the number of *Pseudomonas aeruginosa* bacteria in the feces of the experimental animals was measured. A *Pseudomonas-aeruginosa*-selective medium (Pseudomonas Cetrimide agar plate; Oxoid) was used to prevent interference with other contaminating bacteria in the measurement of the number of *Pseudomonas aeruginosa* bacteria in this example. The sample was spread on the selective medium and cultured at 37° C. for 18 to 24 hr. Colonies presumed to be *Pseudomonas aeruginosa* were isolated from the selective medium, after which *Pseudomonas aeruginosa* was identified through polymerase chain reaction (PCR) (the case where the number of colonies identified as *Pseudomonas aeruginosa* through PCR is $10^2$ cfu/ml or more=2, the case where the number of colonies identified as *Pseudomonas aeruginosa* through PCR is $10^1 \sim 10^2$ cfu/ml=1, and the case where the number of colonies identified as *Pseudomonas aeruginosa* through PCR is $10^0 \sim 10^1$ cfu/ml=0). The results are shown in Table 2 below.

TABLE 2

Results of measurement of number of *Pseudomonas aeruginosa* bacteria (mean)

| | Day | | | | | |
|---|---|---|---|---|---|---|
| | D 9 | D 10 | D 11 | D 12 | D 13 | D 14 |
| Control group (not administered with bacteriophage) | 1.1 | 1.0 | 1.2 | 1.2 | 1.1 | 1.3 |
| Experimental group (administered with bacteriophage) | 0.2 | 0.2 | 0.1 | 0 | 0 | 0 |

As is apparent from the above results, it can be concluded that the bacteriophage Pse-AEP-3 of the present invention is very effective in the treatment of diseases caused by *Pseudomonas aeruginosa*.

Example 6: Treatment 2 of Infectious Disease Caused by *Pseudomonas aeruginosa* Using Bacteriophage Pse-AEP-3

The therapeutic effect of the bacteriophage Pse-AEP-3 on diseases caused by *Pseudomonas aeruginosa* was evaluated as follows. 40 of 8-week-old mice were divided into a total of 2 groups of 20 mice per group, after which subgroups of 5 mice each were separately reared in individual experimental mouse cages, and the experiment was performed for 7 days. On the second day of the experiment, 0.1 ml of a *Pseudomonas aeruginosa* suspension was administered to all mice through intraperitoneal injection. The administered *Pseudomonas aeruginosa* suspension was prepared as follows. Specifically, *Pseudomonas aeruginosa* was cultured at 37° C. for 18 hr in a TSB medium, and only the cells were recovered, and the recovered cells were suspended in saline (pH 7.2) at a concentration of $5\times10^9$ cfu/ml. At 2 hr after administration of *Pseudomonas aeruginosa*, $10^9$ pfu of bacteriophage Pse-AEP-3 was administered through intraperitoneal injection to mice in the experimental group (administered with the bacteriophage solution). 0.1 ml of saline was administered through intraperitoneal injection to mice in the control group (not administered with the bacteriophage solution). Both the control and experimental groups were equally fed with feed and drinking water. Whether or not the mice survived was observed daily starting from the administration of *Pseudomonas aeruginosa* until the end of the test. The results are shown in Table 3 below.

TABLE 3

Results of measurement of survival rate (%)

| | Day after bacteria administration | | | | | |
|---|---|---|---|---|---|---|
| | D 0 | D 1 | D 2 | D 3 | D 4 | D 5 |
| Control group (not administered with bacteriophage solution) | 100 | 75 | 35 | 10 | 10 | 10 |
| Experimental group (administered with bacteriophage solution through intraperitoneal injection) | 100 | 95 | 95 | 95 | 95 | 95 |

As is apparent from the above results, it can be concluded that the bacteriophage Pse-AEP-3 of the present invention is very effective in the treatment of infectious diseases caused by *Pseudomonas aeruginosa*.

While the present invention has been particularly shown and described with reference to exemplary embodiments thereof, those skilled in the art will appreciate that the specific description is only a preferred embodiment, and that the scope of the present invention is not limited thereto. It is therefore intended that the scope of the present invention be defined by the claims appended hereto and their equivalents.

[Accession number]
Name of Depositary Authority: KCTC
Accession number: KCTC 13165BP
Accession date: 2016 Nov. 29

---

The invention claimed is:

1. A method of suppressing a disease caused by a bacterial strain of *Pseudomonas aeruginosa* and alleviating the pathological condition of the disease caused by the bacterial strain of *Pseudomonas aeruginosa*, comprising:
administering to an animal other than a human a composition comprising *Podoviridae* bacteriophage Pse-AEP-3 having a genome set forth by the nucleic acid sequence of SEQ ID NO: 1 and deposited as accession number KCTC 13165BP, which has an ability to specifically kill the bacterial strain of *Pseudomonas aeruginosa*, and wherein the disease is urinary tract infections, wound infections, bacteremia or endocarditis.

* * * * *